US010253362B2

United States Patent
Yoshida et al.

(10) Patent No.: US 10,253,362 B2
(45) Date of Patent: Apr. 9, 2019

(54) DNA TRANSPORT CONTROL DEVICE AND METHOD FOR PRODUCING SAME, AS WELL AS DNA SEQUENCING DEVICE

(71) Applicant: Hitachi High-Technologies Corporation, Minato-ku, Tokyo (JP)

(72) Inventors: Hiroshi Yoshida, Tokyo (JP); Rena Akahori, Tokyo (JP); Yasuhiko Tada, Tokyo (JP); Shohei Terada, Tokyo (JP); Takanobu Haga, Tokyo (JP); Takashi Anazawa, Tokyo (JP)

(73) Assignee: Hitachi High-Technologies Corporation, Tokyo (JP)

( * ) Notice: Subject to any disclaimer, the term of this patent is extended or adjusted under 35 U.S.C. 154(b) by 247 days.

(21) Appl. No.: 15/029,712

(22) PCT Filed: Nov. 4, 2014

(86) PCT No.: PCT/JP2014/079162
§ 371 (c)(1),
(2) Date: Apr. 15, 2016

(87) PCT Pub. No.: WO2015/068673
PCT Pub. Date: May 14, 2015

(65) Prior Publication Data
US 2016/0244823 A1    Aug. 25, 2016

(30) Foreign Application Priority Data

Nov. 8, 2013   (JP) .................................. 2013-232476

(51) Int. Cl.
*C12Q 1/68* (2018.01)
*C12Q 1/6869* (2018.01)
(Continued)

(52) U.S. Cl.
CPC .......... *C12Q 1/6869* (2013.01); *C12Q 1/6872* (2013.01); *G01N 33/48721* (2013.01); *G01N 2015/0038* (2013.01)

(58) Field of Classification Search
None
See application file for complete search history.

(56) References Cited

U.S. PATENT DOCUMENTS

2010/0210742 A1    8/2010   Iyoda et al.

FOREIGN PATENT DOCUMENTS

| JP | 8-248198 A | 9/1996 |
| JP | 2009-57519 A | 3/2009 |

(Continued)

OTHER PUBLICATIONS

T. Yamamoto et al., "Block Copolymer Permeable Membrane with Visualized High-Density Straight Channels of Poly(ethylene oxide)," Advanced Functional Materials, vol. 21, No. 5 (Feb. 2011), pp. 918-926.

(Continued)

*Primary Examiner* — Samuel C Woolwine
(74) *Attorney, Agent, or Firm* — Crowell & Moring LLP

(57) ABSTRACT

The purpose of the present invention is to provide a DNA transport control device having excellent reliability and durability, and a DNA sequencing device that uses the DNA transport control device. The present invention provides a DNA transport control device having a nanopore which allows for the passage of only the DNA strand of a single molecule, and a DNA sequencing device that uses the DNA transport control device. The DNA transport control device is characterized by the following: including a base material having openings and a thin film a block copolymer formed on the base material; the thin film including microdomains that are formed as a result of self-assembly of the block copolymer and that penetrate the thin film, and a matrix surrounding the microdomains; and the nanopore being formed from one opening in the base material and a single microdomain.

12 Claims, 12 Drawing Sheets

(51) Int. Cl.
*G01N 33/487* (2006.01)
*C12Q 1/6872* (2018.01)
*G01N 15/00* (2006.01)

(56) References Cited

FOREIGN PATENT DOCUMENTS

| WO | WO 2011/046706 A1 | 4/2011 |
| WO | WO 2013/011879 A1 | 1/2013 |
| WO | WO 2013/012881 A2 | 1/2013 |
| WO | WO 2013/140316 A2 | 9/2013 |
| WO | WO 2014/208184 A1 | 12/2014 |

OTHER PUBLICATIONS

F. Haque et al., "Solid-state and biological nanopore for real-time sensing of single chemical and sequencing of DNA," Nano Today, vol. 8, No. 1 (Feb. 2013), pp. 56-74.

S. Y. Yang et al, "DNA-Functionalized Nanochannels for SNP Detection," Nano Letters, vol. 11, No. 3 (Feb. 2011), pp. 1032-1035.
International Search Report (PCT/ISA/210) issued in PCT Application No. PCT/JP2014/079162 dated Feb. 3, 2015 with English-language translation (four (4) pages).
Japanese-language Written Opinion (PCT/ISA/237) issued in PCT Application No. PCT/JP2014/079162 dated Feb. 3, 2015 (five (5) pages).
M. Wanunu, "Nanopores: A journey towards DNA sequencing," Physics of Life Reviews, vol. 9, (May 2012), pp. 125-158.
T. Z. Butler et al., "Single-molecule DNA detection with an engineered MspA protein nanopore," Proceedings of the National Academy of Sciences, vol. 105, No. 52 (Dec. 2008), pp. 20647-20652.
D. Krapf et al., "Fabrication and Charaterization of Nanopore-Based Electrodes with Radii down to 2nm," Nano Letters, vol. 6, No. (2006), pp. 105-109.
C. Park et al. "Enabling nanotechnology with self assembled block copolymer patterns," Polymer, vol. 44, No. 22 (Jul. 2003), pp. 6725-6760.
Y. Tian et al., "Synthesis, Nanostructures, and Functionality of Amphiphilic Liquid Crystalline Block Copolymers with Azobenzene Moieties," Macromolecules, vol. 35, (Mar. 2002), pp. 3739-3747.
German-language Office Action issued in counterpart German Application No. 11 2014 004 341.9 dated Apr. 5, 2017 (Three (3) pages).

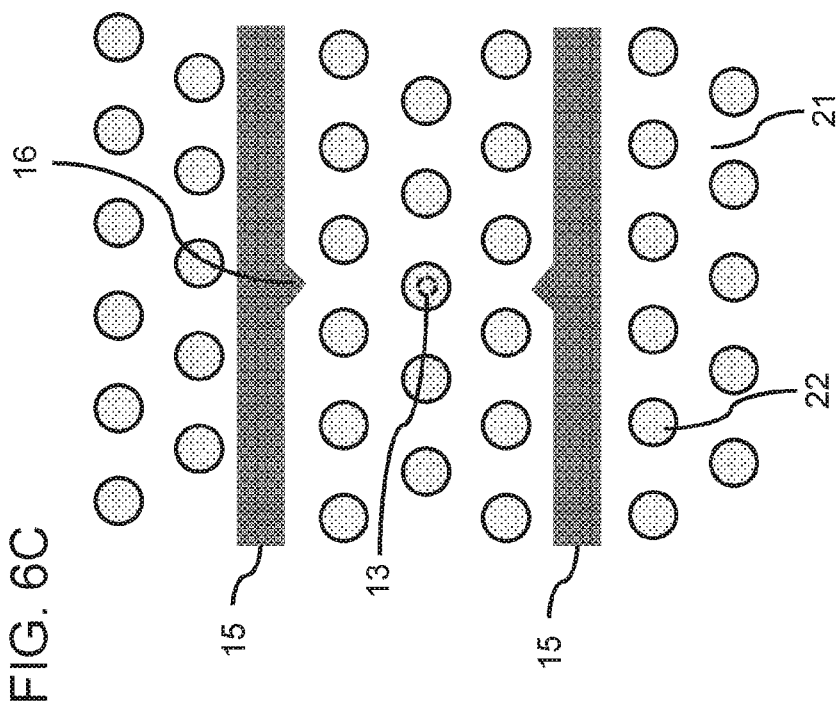
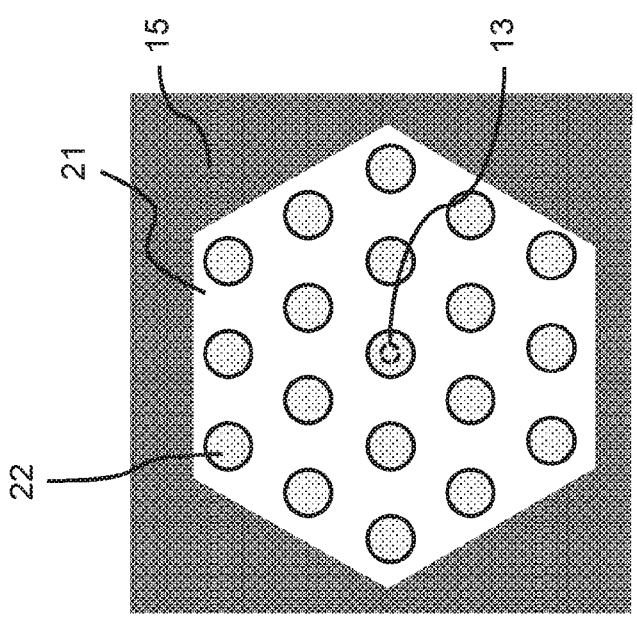
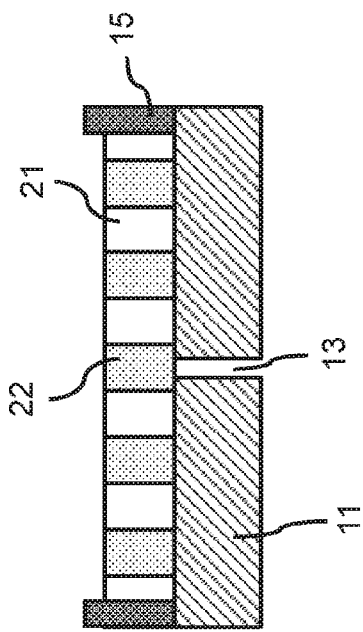

PEO$_{114}$-b-PMA(Az)$_{34}$

100nm

PEO$_{40}$-b-PMA(Az)$_{84}$

30nm

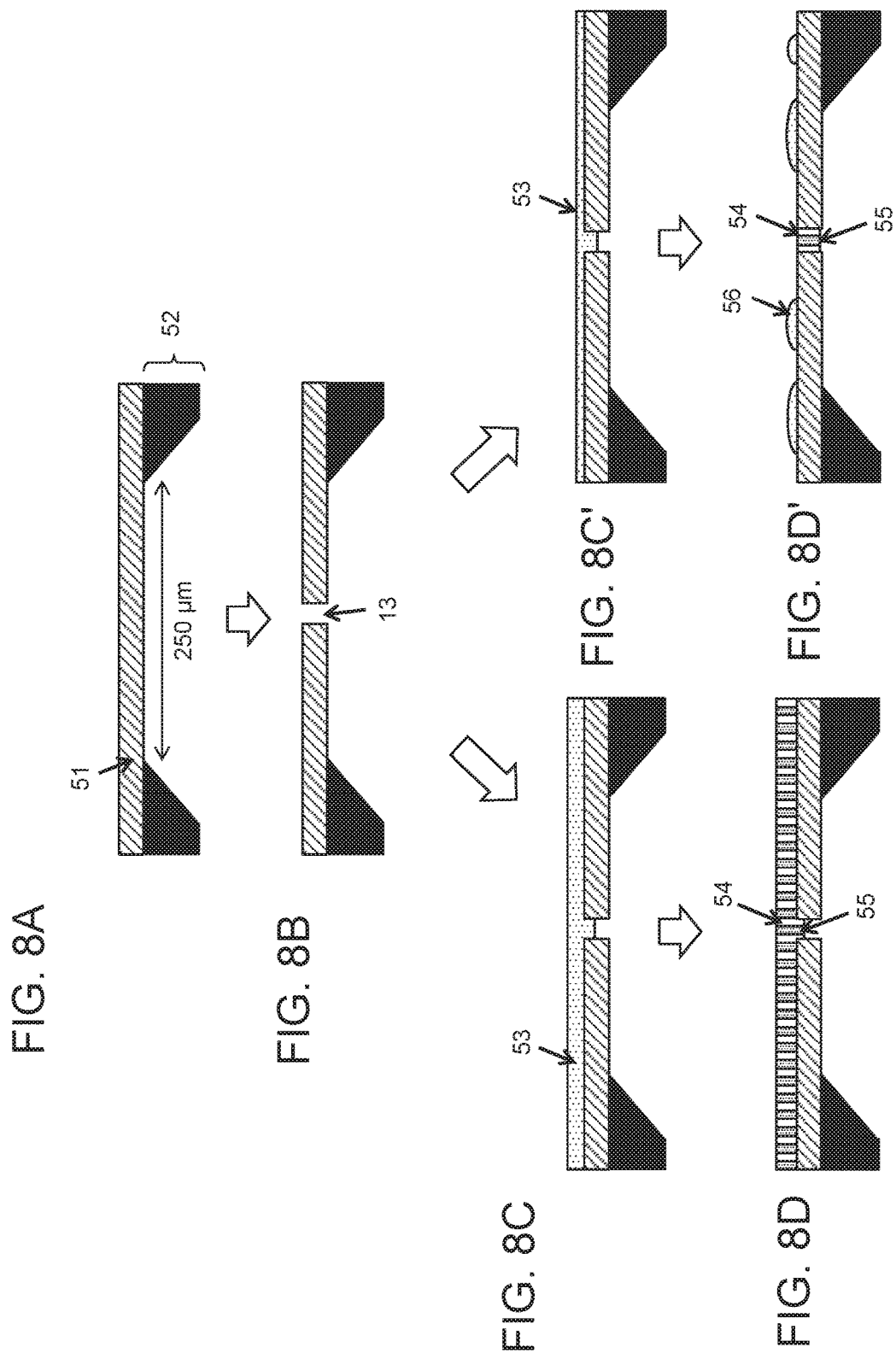

FIG. 9A
FIG. 9B
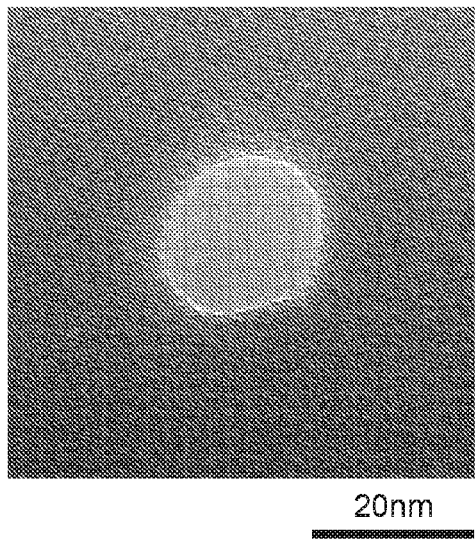
20nm
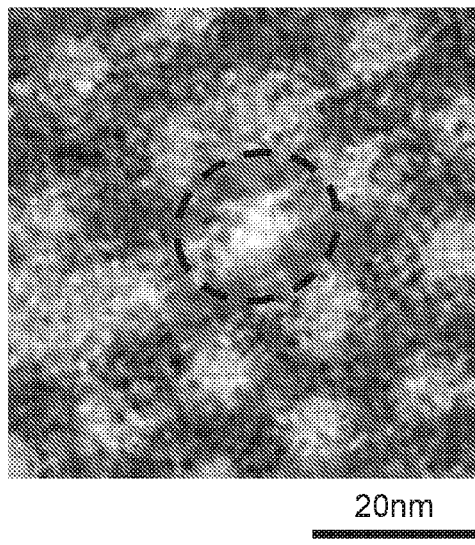
20nm

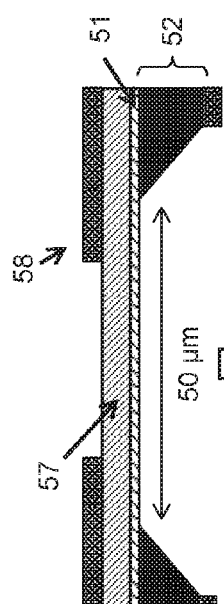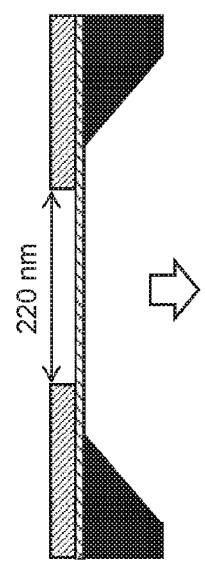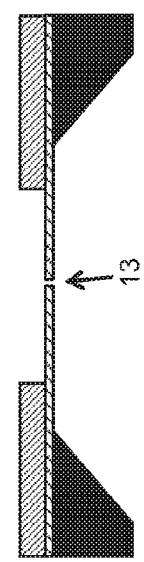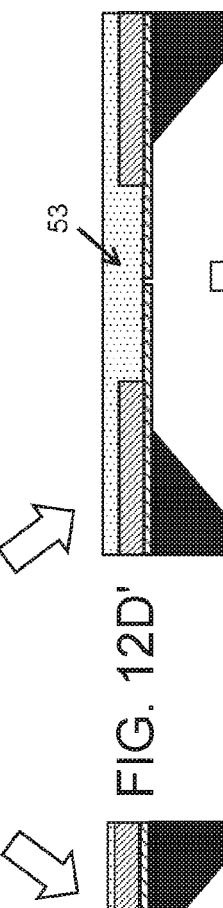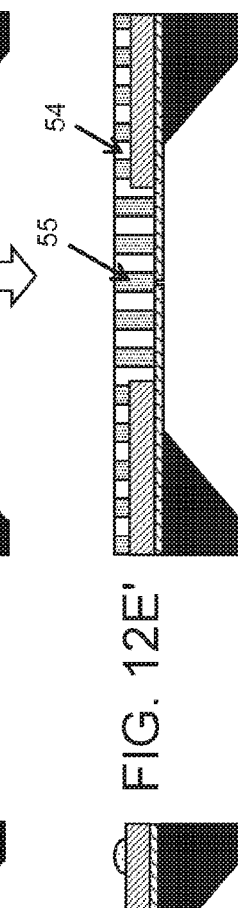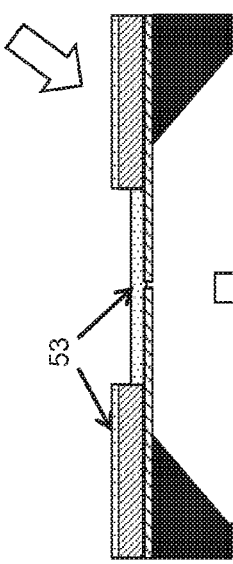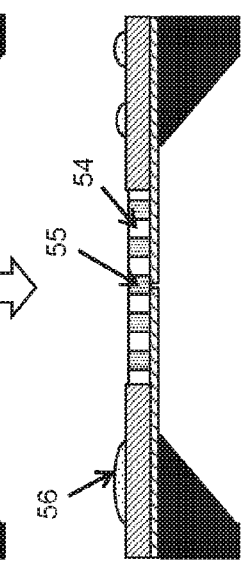
FIG. 12A  FIG. 12B  FIG. 12C  FIG. 12D'  FIG. 12E'  FIG. 12D  FIG. 12E

DNA TRANSPORT CONTROL DEVICE AND METHOD FOR PRODUCING SAME, AS WELL AS DNA SEQUENCING DEVICE

TECHNICAL FIELD

The present invention relates to a device to control the transport of DNA strands and a method for producing the same. The present invention also relates to a DNA sequencing device to read base sequences of DNA strands.

BACKGROUND ART

A nanopore DNA sequencer provided with a pore of a nanometer size (nanopore) which is almost equal to the size of DNA, and a sensor to read base sequences in the neighborhood or the inner portion thereof has paid attention as a method for determining base sequences of deoxyribonucleic acid (DNA) without using a reagent (NPL 1).

The nanopore DNA sequencer sequentially identifies base species by directly measuring changes in a physical quantity based on each base species contained in a DNA strand when the DNA strand passes through the nanopore. The sequencer is capable of high speed decoding, further does not amplify template DNA by an enzyme and does not use labeling substances such as fluorescent substances, and is thus expected to lead to high throughput, low costs and decoding of long base length. As changes in physical quantity based on base species, proposed are changes in tunnel current through a DNA strand, the charge amount of the DNA strand, and ion current passing through a nanopore and the like when DNA passes through the nanopore, and a method for measuring these and the like.

In nanopore DNA sequencing, a nanopore plays a role of controlling the transport of a single molecule of DNA strand. There are two major problems as follows. The first problem is to provide a method for stably producing a nanopore the size of which allows the passage of only a single molecule of DNA strand on a large scale. The second problem is to delay the velocity of a DNA strand passing through a nanopore to the velocity enough to read the base sequence of DNA. As a method for solving the above-mentioned problems, the following two approaches have been proposed.

The first approach is a method using a micropore formed by modified protein as a nanopore (bionanopore). It has been reported that a protein having a fine pore through which a single molecule of DNA strand selectively passes is produced and allowed to support the inside of membrane protein, thereby being able to control the transport of DNA (NPL 2). The second approach is a method in which a nanopore is produced in a solid thin film by a top-down means using a semiconductor micromachining process (solid-state nanopore). As one of typical production methods, there is a method in which a region containing a thin film insulator is provided on a semiconductor substrate and an electron beam is irradiated to form a pore as described in NPL 3. A fine pore with 10 nm or less can be formed by controlling the energy, area irradiated and current of the electron beam.

In the meantime, as a method for forming a very fine pattern within the process limitation of photolithography or less, a block copolymer lithography method using microphase separation, which is the self-assembly process of a block copolymer, has paid attention as a next-generation semiconductor lithography technique (NPL 4). Cylindrical and linear/spatial microdomains are formed by self-assembly by microphase separation of poly(styrene-b-methylmethacrylate) (PS-b-PMMA), a type of block copolymer, and a pattern with about 10 nm to 100 nm can be obtained by removing domains containing polymethylmethacrylate by etching. A method for processing a substrate using the microdomains as a mask has been considered.

Further, when a block copolymer containing a hydrophobic polymer chain and a hydrophilic polymer chain is used and fine cylinders containing the hydrophilic polymer chain are formed by self-assembly to penetrate a block copolymer thin film, it is shown that a dye molecule permeates the fine cylinders (NPL 5).

CITATION LIST

Non-Patent Literature

NPL 1: Meni Wanune, Physics of Life Reviews (2012) Vol. 9, 125-158
NPL 2: Tom Z. Butler et al., Proceedings of the National Academy of Sciences (2008) Vol. 105, No. 52, 20647-20652
NPL 3: Diego Krapf et al., Nano Letters (2006) Vol. 6, No. 1, 105-109
NPL 4: Cheolmin Park et al., Polymer (2003) Vol. 44, No. 22, 6725-6760
NPL 5: Takashi Yamamoto et al., Advanced Functional Materials (2011) Vol. 21, 918-926

SUMMARY OF INVENTION

Technical Problem

The bionanopore, the first approach to solve the problems of nanopores, lacks stability and reliability because of using a biological molecule, and thus has a problem of being unable to be repeatedly used for a prolonged time. Further, it is also difficult to arrange nanopores in parallel for fast reading. In addition, the solid-state nanopore, the second approach, has a problem in that even when applying a cutting-edge semiconductor processing technique, it is difficult to produce fine pores required to sufficiently delay the passage velocity of a DNA strand, i.e. pores with a diameter of single nanometer order, on a large scale. Further, in order to reduce the distribution of the transport velocity of a DNA strand, it is required to control the diameter of a pore with a high degree of accuracy; however, it is difficult to process a size of single nanometer order with repeatability by the current top-down micromachining technique.

Meanwhile, as a method for producing a nanopore structure with repeatability on a large scale, the use of cylindrical microdomains obtained by the self-assembly of a block copolymer is thought to be a rational method. The cylindrical microdomains however have a densely arranged hexagonal structure, and thus a device with a single nanopore or nanopores arranged at a predetermined interval required as a DNA transport control device cannot be obtained. In addition, even when cylindrical microdomains are removed by etching to produce a pore opened, it is difficult to sufficiently delay the transport velocity of a DNA strand as is the case with the solid-state nanopore. Therefore, a case using the self-assembly of a block copolymer to form a nanopore through which a DNA strand is allowed to pass has not been known until now.

An object of the present invention is to find a method for easily obtaining a nanopore which has a minute size allowing the permeation of only a single uniform molecule of DNA strand, and further which can delay the transport velocity of a DNA strand to the velocity at which a base sequence can be read by utilizing the self-assembly of a block copolymer, and to provide a DNA transport control device with excellent reliability and durability using such a method.

Solution to Problem

As a result of investigations, the present inventors thought of, by preparing a base material with an opening, producing a thin film of a block copolymer on the base material, and self-assembling it, forming a passage route for DNA (nanopore) including a cylindrical microdomain formed by self-assembly and the opening of the base material, and producing a DNA transport control device.

A DNA transport control device of the present invention has a nanopore which allows the passage of only a single molecule of DNA strand, the device including: a base material having an opening; and a thin film of a block copolymer formed on the base material, wherein the thin film includes microdomains which are formed by self-assembly of the block copolymer and penetrate the thin film, and a matrix surrounding the microdomains, and the nanopore includes one opening in the base material and a single microdomain.

The present description encompasses the contents described in the present description and/or drawings of Japanese patent application No. 2013-232476, to which this application claims priority.

Advantageous Effects of Invention

The DNA transport control device of the present invention has a nanopore which can delay the transport velocity of a DNA strand to the velocity at which a base sequence can be read, and a method for producing the same is also easy. The technique of the present invention can stably produce a highly accurate nanopore and is thus very useful for producing a DNA sequencing device.

BRIEF DESCRIPTION OF DRAWINGS

FIGS. 6A to 6C are diagrams describing a method for controlling the arrangement of cylindrical microdomains 22 by the graphoepitaxy effect.

FIGS. 8A to 8D' are diagrams schematically illustrating a process for producing a DNA transport control device by the first embodiment.

FIGS. 9A and 9B are a TEM observation image of the base material pore, and an overlay image of the base material pore and cylindrical microdomains by STEM observation.

FIGS. 12A to 12E' are diagrams schematically illustrating a process for producing a DNA transport control device by the second embodiment.

DESCRIPTION OF EMBODIMENTS

DNA Sequencing Device

Figure 1:
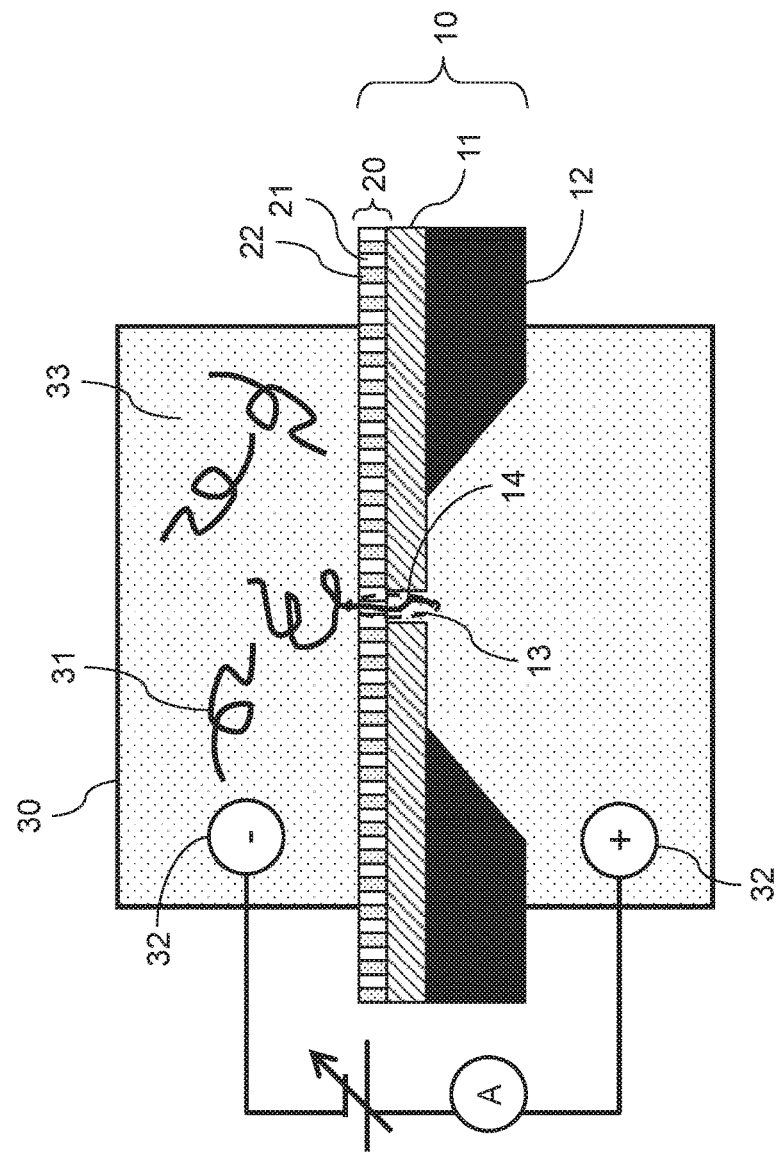
FIG. 1 is a schematic diagram illustrating the cross-sectional structure of a DNA sequencing device using the DNA transport control device 10 of the present invention.

FIG. 1 is a schematic diagram illustrating a cross-sectional structure of a DNA sequencing device using the DNA transport control device of the present invention. Two solution cells 30 containing an electrolyte aqueous solution 33 are communicated via a passage route 14 (nanopore) in the DNA transport control device 10. Here, the DNA strand 31, a sample, the sequence of which should be read, is contained in one solution cell 30. The passage route 14 for DNA strands in the DNA transport control device 10 includes a base material pore 13 and a cylindrical microdomain 22. In addition, an electrode 32 is installed in each solution cell 30, and the DNA strand 31 passes through the passage route 14 in the DNA transport control device 10 by applying voltage to two poles.

When a sensor is required in order to read a base sequence when the DNA strand 31 passes through the passage route 14 in the DNA transport control device 10, the sensor is installed in the front or back of the DNA transport control device 10, or in the inner portion thereof. In FIG. 1, the sensor is omitted for simplification. A means to read DNA sequences and the constitution of a sensor for that are not particularly restricted. Various conventionally proposed methods can be used such as methods for measuring changes in tunnel current through a DNA strand, the charge amount of the DNA strand, the blocked degree of ion current passing through the passage route and the like when the DNA strand 31 passes through the passage route 14 for DNA strands. A method for measuring the chemical composition of a DNA strand passing through the passage route 14 by spectral means such as Raman scattering and infrared absorption can be used. When spectral means are used, an excitation method by a locally enhanced optical field such as plasmon is preferably applied to obtain spatial resolution corresponding to a base size. In the device of the present invention, a sensor which can measure base sequences based on various methods can be appropriately used.

(DNA Transport Control Device)

The DNA transport control device 10 of the present invention has a structure in which a block copolymer thin film 20 is produced on a base material 11 having a base material pore 13 opened thereon. In the present description, having the block copolymer thin film 20 on the base material 11 is a concept containing not only when the block copolymer thin film 20 exists on the planar surface of the upper surface or lower surface, or both surfaces of the base material 11, but also when the block copolymer thin film 20 exists only in the base material pore 13, and when the block copolymer thin film 20 exists on the planar surface of the upper surface or lower surface or both of the base material 11 and further in the base material pore 13. The block copolymer thin film 20 has cylindrical microdomains 22 penetrating the thin film formed by self-assembly by microphase separation. The shape of microdomains 22 is desirably cylindrical as shown in the figure, but can be non-cylindrical shape as long as the microdomains are formed to penetrate the thin film.

A base material pore 13 with a diameter D is opened in the base material 11, and the diameter D is preferably 1 nm or more and further preferably 30 nm or less. Particularly when the first embodiment described below is applied, the diameter D is preferably 5 nm or more and 25 nm or less. In addition, when the second embodiment described below is applied, the diameter D is particularly preferably 1 nm or more and 10 nm or less.

The film thickness of the base material 11 is preferably 100 nm or less and particularly 50 nm or less so that a fine pore can be opened, and further preferably 0.3 nm or more when applied to a sequence reading method using blockage current, and preferably 10 nm or more to have sufficient strength in the cases other than the above.

A material for the base material 11 is not particularly limited as long as a base material pore 13 can be opened, and silicon nitride ($Si_3N_4$ as a typical composition), silicon oxide ($SiO_2$) and hafnium oxide ($HfO_2$) are particularly preferred due to corrosive resistance to the electrolyte solution 33 and an easy processing for opening a pore. In addition, the base materials 11 can be used individually, but it is preferred that a support substrate 12 be provided to improve the hardness and handleability of the base material 11 as shown in FIG. 1. Further, in order to improve the affinity between the base material 11 and the block copolymer thin film, a polymer chain and a coupling agent can be grafted on the surface of the base material 11 for chemical modification.

The shape of the base material pore 13 is preferably circular, but is not necessarily exact circle and can be in the shape of ellipse or polygon or in a distorted shape thereof. When the base material pore 13 forms a figure other than the shape of exact circle, the diameter D of the base material pore 13 means the diameter of the exact circle drawn to have the area in the figure.

The base material 11 can be produced according to an existing method as disclosed in for example JP H8-248198 A. For example, a silicon nitride or silicon oxide film to be a base material 11 is formed on a silicon wafer to be a support substrate 12, and a base material can be then produced by opening a window by removing the silicon wafer on the back by an anisotropic etching technique using for example a TMAH solution or a KOH aqueous solution.

Various existing semiconductor processing means can be applied to open a base material pore 13, and most suitable method can be adopted in view of a processing size and processing time. For example, focused ion beam (FIB) processing by a particle beam such as gallium ion or helium ion, electron beam (EB) processing by a focused electron beam, processing by photolithography and the like can be adopted. Direct processing techniques such as FIB processing and EB processing are suitable to open a single base material pore 13. Meanwhile, when a device capable of parallel reading by arraying base material pores 13 is produced, processing by photolithography is suitable in terms of time required for processing.

(Block Copolymer Thin Film)

Figure 2B:
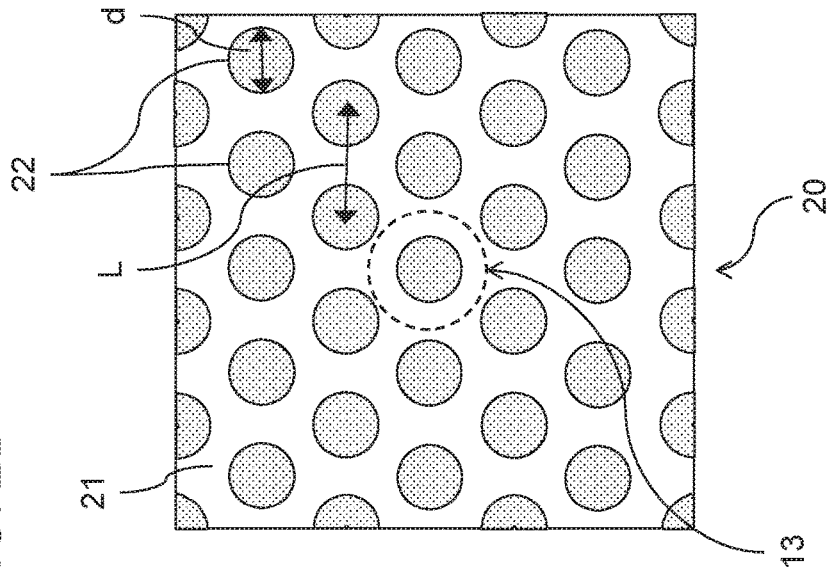
FIGS. 2A and 2B are outline diagrams illustrating the structure of a block copolymer thin film 20.
Figure 2A:
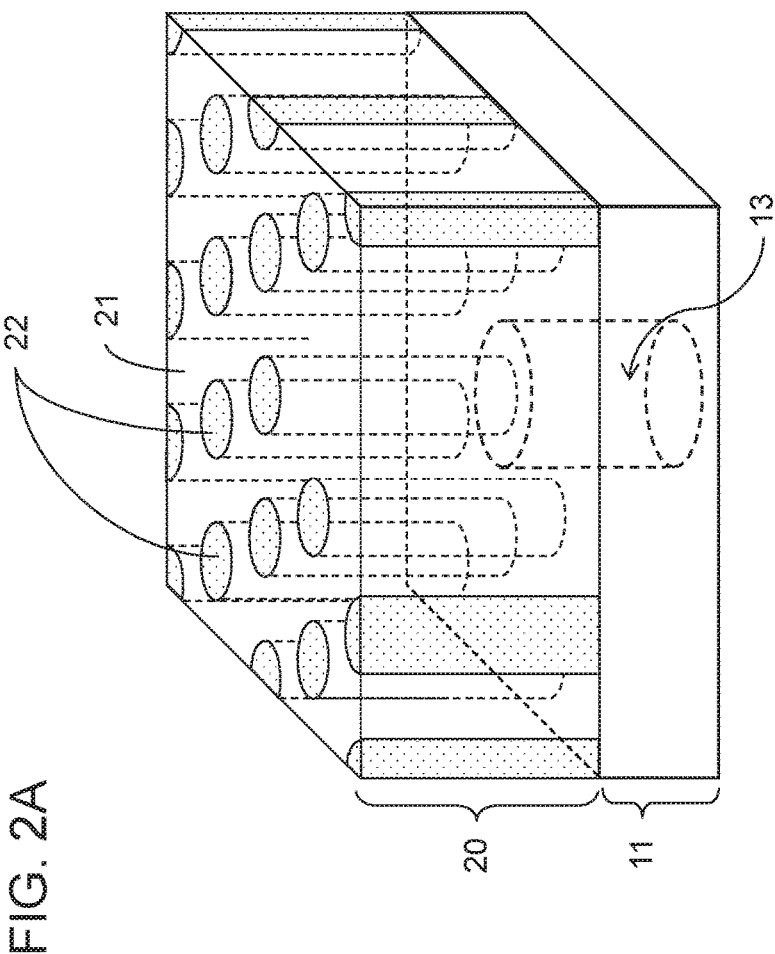

FIGS. 2(a) and 2(b) are outline diagrams illustrating the structure of a block copolymer thin film 20. As shown in FIGS. 2(a) and 2(b), the block copolymer thin film 20 has a structure in which cylindrical microdomains 22 are formed in the matrix 21 (continuous phase) by microphase separation. The block copolymer thin film is formed on the surface of the base material 11 having the base material pore 13. In FIG. 2(a), parts of cylindrical microdomains 22 are omitted to clearly illustrate the positional relationship between the base material pore 13 and the cylindrical microdomains 22. In FIG. 2(a), the block copolymer thin film 20 is produced only on the surface of the base material 11, but a block copolymer thin film 20 can be formed on both surfaces of the base material 11 and in the inner portion of the base material pore 13 as described below.

The cylindrical microdomains 22 are arranged and distributed in the matrix 21 and further oriented in the direction of penetration of the block copolymer thin film 20. As shown in FIG. 2 (b), the cylindrical microdomains 22 form a regularly arranged pattern to make a hexagonal close-packed structure on the level surface of the block copolymer thin film 20.

In FIG. 1 and FIGS. 2(a) and 2(b), the diameter D of the base material pores 13 is shown to be greater than the diameter d of cylindrical microdomains 22, which shows the constitution corresponding to the first embodiment of the present invention described below. In the second embodiment, the diameter D of a base material pore 13 is smaller than the diameter d of cylindrical microdomains 22. Because it can be said that the diameter d and the center-to-center spacing L of cylindrical microdomains 22 are almost determined depending on a block copolymer to be used, by measuring the diameter d and center-to-center spacing L of each block copolymer in advance, the size of the opening of a base material pore 13 can be determined based on the values, or a suitable block copolymer can be selected by the size of the opening of a base material pore 13.

Figure 3B:
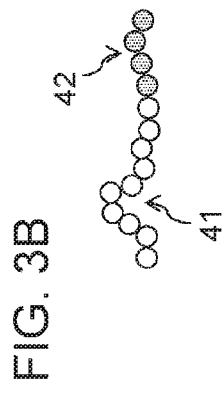
FIGS. 3A to 3C are diagrams schematically enlarging the constituent units of a block copolymer thin film 20.
Figure 3A:
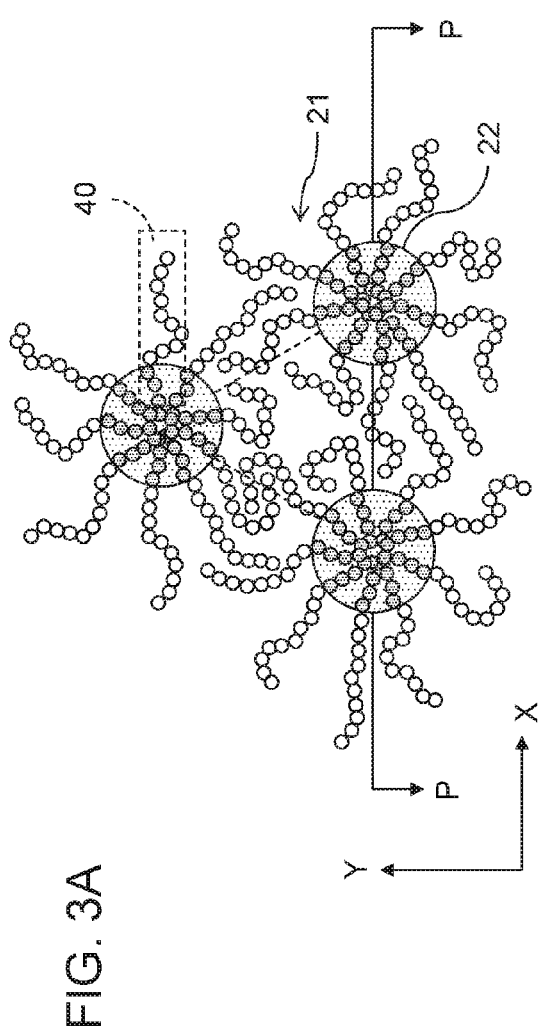
Figure 3C:
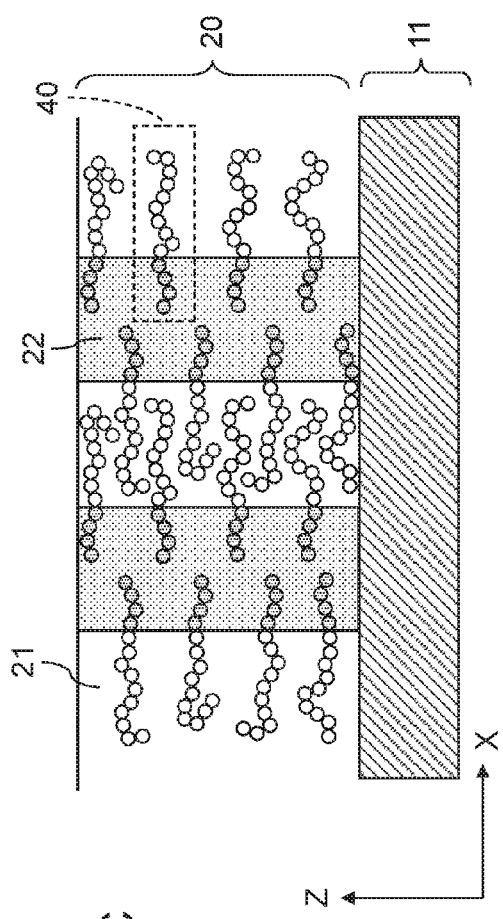

Next, with reference to FIGS. 3(a) to 3(c), the microphase separation structure of a block copolymer thin film 20 will be described. FIGS. 3(a) to 3(c) are diagrams schematically enlarging the constituent units of a block copolymer thin film 20. The block copolymer thin film 20 is formed from a block copolymer 40 individually or using it as a main component. When the block copolymer 40 is a diblock copolymer, its molecule has a chemical structure in which a hydrophobic polymer chain 41 and a hydrophilic polymer chain 42 are bound at each terminal as shown in FIG. 3(b).

The volume of the hydrophobic polymer chain 41 in the block copolymer 40 is greater than the volume of the hydrophilic polymer chain 42, which is preferred because the block copolymers 40 are easily arranged so that the binding point of both polymer chains will form the side of the cylinder as shown in FIG. 3(c). The matrix 21 having the hydrophobic polymer chain 41 as the main component and the cylindrical microdomains 22 having the hydrophilic polymer chain 42 as the main component are formed by self-assembly by microphase separation using the binding site of the hydrophobic polymer chain 41 and the hydrophilic polymer chain 42 as a border.

It is only required that a block copolymer 40 be synthesized by a suitable method, and a synthetic method by which a molecular weight distribution is made as small as possible, for example a living polymerization method and an atom transfer radical polymerization (ATRP) method, is preferably used to improve the regularity of a microphase separation structure. The block copolymer 40 can be an AB-type diblock copolymer in which a hydrophobic polymer chain 41 and a hydrophilic polymer chain 42 are bound at each terminal as shown in FIG. 3(b), or can be an ABA-type triblock copolymer. In addition, the block copolymer has a third polymer chain and can be an ABC-type block copolymer containing three or more polymer chains. Further, the block copolymer can be a block copolymer in which polymer chains are bound in series as described above and further can be a star-type block copolymer in which polymer chains are bound at a point.

The hydrophilic polymer chain 42 constituting a block copolymer 40 includes those containing polyethylene oxide (PEO), polylactic acid (PLA), polyacrylamide (e.g. N,N-dimethylacrylamide), polyhydroxyalkylmethacrylate (e.g. polyhydroxyethylmethacrylate (PHEMA) etc.), or an ionic polymer (e.g. a polymer of unsaturated carboxylic acid such as polyacrylic acid or polyacrylic methacrylic acid, nucleic acid or a salt thereof), and particularly those containing polyethylene oxide, polylactic acid or polyhydroxyethylmethacrylate.

The hydrophobic polymer chain 41 constituting a block copolymer 40 includes those containing polystyrene (PS), polyalkylmethacrylate (e.g. polymethylmethacrylate (PMMA)), polyvinylpyridine, polyalkylsiloxane (e.g. polydimethylsiloxane), polyalkyldiene (e.g. polybutadiene) or the like. Particularly, the hydrophobic polymer chain 41 is preferably those having a side chain which is a rod-shaped molecule having a mesogenic group to express liquid crystallinity (liquid crystalline side chain). The mesogenic group includes groups having a skeleton based on azobenzene, stilbene, benzylideneaniline, biphenyl, naphthalene or cyclohexane. In addition, a spacer group bound to the mesogenic group in such a liquid crystalline side chain includes alkyl, alkoxy or alkoxyalkyl or the like. The spacer group is preferably a straight chain and the number of carbons thereof is preferably 4 or more. Particularly, the number of carbons in the spacer group existing between the main chain of a hydrophobic polymer chain and the mesogenic group is more preferably 5 or more, particularly 8 or more and especially 10 or more. The hydrophobic polymer chain 41 having such a side chain includes those in which the alkyl moiety in polyalkylmethacrylate is partially or completely substituted with such a liquid crystalline side chain. A hydrophilic polymer chain 42 to be combined with a hydrophobic polymer chain 41 having the liquid crystalline side chain is particularly preferably polyethylene oxide.

When a liquid crystalline side chain is introduced into a hydrophobic polymer chain 41, there are advantages of being easy to obtain a structure in which cylindrical microdomains 22 are perpendicular to a block copolymer thin film 20 and are oriented in the direction of penetration of the thin film, and of being able to increase the ratio L/d of the center-to-center spacing L of cylindrical microdomains 22 and the diameter d of cylindrical microdomains 22.

In a liquid crystalline block copolymer in which a liquid crystalline side chain is introduced into a hydrophobic polymer chain 41, a matrix 21 containing the hydrophobic polymer chain 41 having a liquid crystalline site expresses a liquid crystalline phase. When the liquid crystalline phase is expressed, the liquid crystalline side chain is homeotropically aligned to the upper surface of a block copolymer thin film 20 (i.e. free surface). Due to the effect, cylindrical microdomains 22 are perpendicular to the surface of the block copolymer thin film 20 and are easily oriented in the direction of penetration of the thin film. The orientation of cylindrical microdomains 22 varies depending on the film thickness of a block copolymer thin film 20, process temperature during self-assembly, the surface state of a base material and the like in many cases, and the control thereof can be associated with difficulty. By using a liquid crystalline block copolymer, cylindrical microdomains 22 are easily oriented perpendicular to a block copolymer thin film 20 and the orientation in the direction of penetration of the thin film can be obtained.

The self-assembled structure of a block copolymer is prescribed by the composition ratio of blocks, i.e. the ratio of volume occupied by polymer chains constituting a block copolymer. As the composition ratio increases from 0.5 toward 1.0, the self-assembled structure, i.e. the shape of domains, varies from lamellar (plate) to cylindrical and further spherical shapes. In the meantime, it is required that the composition ratio be increased in order to increase the ratio L/d of the center-to-center spacing L and the diameter d of the cylindrical shape with the cylindrical shape maintained. In the case of a simple block copolymer, the maximum value of L/d is thought to be about 2.5 due to a relationship between the above-mentioned composition ratio and domain structure, and when the composition ratio is increased so that the L/d value will be higher, the domain shape varies from cylindrical to spherical shapes. In a liquid crystalline block copolymer in which a liquid crystalline side chain is introduced into a hydrophobic polymer chain, however, this restriction can be considerably relaxed and cylindrical domains with an L/d of above 10 can be also formed. In the case of a hydrophobic polymer chain having a liquid crystalline side chain, this is derived from forming a conformation in which a polymer chain is linearly stretched by the arrangement of liquid crystalline site.

(Delay in Transport Velocity of DNA Strand)

As shown in FIGS. 3(a) to 3(c), cylindrical microdomains 22 containing a hydrophilic polymer chain 42 are arranged in a block copolymer thin film 20 to penetrate the block copolymer thin film 20. The diameter d of the cylindrical microdomains 22 can be controlled in the range of from 1 nm at the minimum to 100 nm at the maximum by the molecular weight of a block copolymer to be used. The block copolymer thin film 20 has a structure in which the hydrophilic cylindrical microdomains 22, i.e. able to contain an aqueous solution, are arranged in a hydrophobic matrix 21, i.e. insoluble in water.

The present inventors diligently investigated and discovered the effect of delaying the transport velocity of a DNA strand, the first effect of the present invention. That is, the present inventors found that a DNA strand passed through cylindrical microdomains 22 immersed in an aqueous solution, and the passage velocity is very slow compared to the transport velocity of a DNA strand in a micropore in which a hydrophilic polymer chain is not filled or in a water-soluble polymer gel in a bulk state, thereby completing the present invention.

Figure 4:
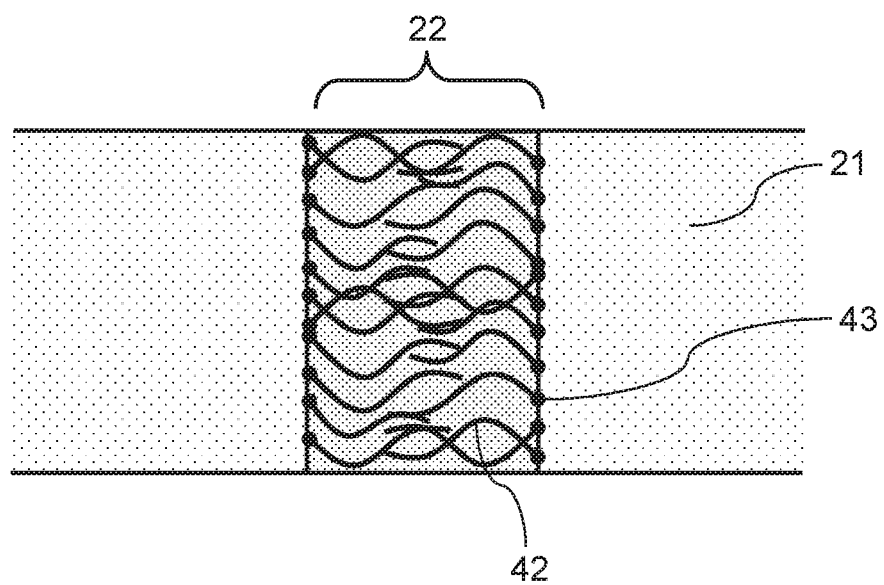
FIG. 4 is a schematic diagram illustrating the structure of a cylindrical microdomain 22.

As schematically shown in FIG. 4, the cylindrical microdomain 22 is surrounded by a hydrophobic matrix 21 and has a structure in which the terminal of the hydrophilic polymer chain 42 filling in the inner portion thereof is fixed at the interface of the cylindrical microdomain 22 and the hydrophobic matrix 21, i.e. the cylindrical side of the cylindrical microdomain. It is believed that the density in the dry state of the hydrophilic polymer chain 42 in the cylindrical microdomain 22 is almost equal to that in the solid state. When a thin film having such a structure is immersed in an aqueous solution, low molecules such as water and an electrolyte contained in the aqueous solution are diffused in the inner portion of the hydrophilic cylindrical microdomains 22. In the meantime, the hydrophilic polymer chain 42 is not considerably swollen because the terminal thereof is fixed to the cylindrical side at the fixing point 43, and the density of the hydrophilic polymer chain 42 in the cylindrical microdomains 22 does not largely decrease. That is, it is expected that the inner portion of the cylindrical microdomains 22 is a fine space filled with a gel with ultrahigh density. It has never been known whether a high molecular weight DNA strand can enter and pass through such a fine space; however, as a result of various investigations, the present inventors eventually found that a DNA strand passed through the inner portion of cylindrical microdomains 22 by providing a potential difference in front and back of the film.

The transport velocity of a DNA strand can be controlled by the diameter d of cylindrical microdomains 22, the height of cylindrical microdomains 22, i.e. the thickness of a block copolymer thin film 20, the density of a hydrophilic polymer chain 42 in cylindrical microdomains 22 and the like. It is required that the diameter d of cylindrical microdomains 22 be controlled in view of a relationship with a base material pore 13 as described below. Meanwhile, the thickness of a block copolymer thin film 20 is optional, and is desirably in the range of from 10 nm or more, particularly 20 nm or more to 500 nm or less, particularly 100 nm or less to stably obtain a structure in which cylindrical microdomains 22 penetrate the film with repeatability.

As the structure of microdomains, a cylindrical shape is most suitable in terms of controlling the DNA transport velocity; however, it has been found that the effect of delaying the transport velocity of a DNA strand is obtained in for example lamellar microdomains oriented to penetrate a thin film and co-continuous domains in various degrees, and the application of those structures is not removed.

(Method for Producing Block Copolymer Thin Film)

A block copolymer thin film 20 which cylindrical microdomains 22 are arranged to penetrate can be produced by the following method.

First, a block copolymer 40 with a predetermined chemical structure and composition is synthesized. For its polymerization reaction, a living polymerization method and an atom transfer radical polymerization (ATRP) method are suitable because the molecular weight, composition and molecular weight distribution can be controlled as described above. Because the shape and size of domains to be obtained and the distance between domains and the like vary depending on the molecular weight of a block copolymer 40 and the molecular weight ratio of a hydrophobic polymer chain 41 and a hydrophilic polymer chain 42 constituting a block copolymer, it is desired that the polymerization reaction be adjusted so that a predetermined structure will be self-assembled.

Next, the obtained block copolymer 40 is dissolved in a solvent and a film is produced on the surface of a base material 11 having a base material pore 13. Here, the solvent is not particularly restricted as long as a block copolymer is uniformly dissolved, and commonly used organic solvents such as toluene and chloroform can be used. Since the block copolymer 40 is amphipathic, a solvent which can uniformly dissolve it does not exist depending on the chemical composition of polymer chains to be combined in some cases. In these cases, a mixed solvent obtained by mixing various solvents can be applied.

For producing a block copolymer thin film 20, means such as spin-coating and dip-coating can be appropriately applied. As described below, there is also constitution in which a block copolymer thin film 20 is arranged on both surfaces of a base material 11 in the embodiment of the present invention, and in such a case, a dip-coating method is suitably applied. The block copolymer thin film 20 can be controlled to have a predetermined film thickness by film-producing conditions such as the concentration of a block copolymer solution, the type of solvent, the number of rotations in the case of spin-coating, and the pulling velocity in the case of dip-coating. In addition, the filling degree of a block copolymer in the inner portion of a base material pore 13 provided on a base material 11 can be also controlled by film-producing conditions.

A block copolymer molecule 40 in a block copolymer thin film 20 produced by the above-mentioned means is in a random state by rapid evaporation of a solvent in many cases. That is, the block copolymer is in a state in which the microphase separation process is frozen halfway, and intended cylindrical microdomains do not exist in the thin film in many cases. Therefore, by the annealing treatment of a block copolymer thin film 20 produced on a base material 11, the microphase separation process can be allowed to proceed and a structure in which cylindrical microdomains are regularly arranged in a block copolymer thin film in a uniform state can be formed.

Here, the annealing treatment is a treatment, by maintaining a block copolymer 40 in a kinetic state in a block copolymer thin film 20, to form a structure in which the free energy of the thin film is minimum. The annealing treatment can be carried out by a method such as heating treatment at the glass transition temperature of polymer chains constituting a block copolymer 40 or more (thermal annealing) or a treatment, by exposing a block copolymer thin film 20 to solvent vapor, to swell the film (solvent annealing).

In the present invention, it is required that cylindrical microdomains 22 be self-assembled to penetrate a block copolymer thin film 20, and the orientation of the cylindrical microdomains 22 can be controlled by an annealing method depending on the type of block copolymer. It is therefore desired that an annealing method be carefully selected depending on the type of block copolymer. When PS-b-PEO, a block copolymer, having polystyrene (PS) as a hydrophobic polymer chain 41 and polyethylene oxide (PEO) as a hydrophilic polymer chain 42 is used, for example, cylindrical microdomains containing PEO can be self-assembled to penetrate the PS-b-PEO thin film by solvent annealing.

When a liquid crystalline block copolymer is used, it is also required to carefully consider the liquid crystal transition temperature. In the liquid crystalline block copolymer, the liquid crystalline section expresses isotropic phases randomly dispersed at its liquid crystal transition temperature or higher and expresses liquid crystallinity by orientation in a fixed direction below its liquid crystal transition temperature. When a liquid crystalline block copolymer is used, therefore, a uniform microphase separation structure can be obtained by first heating to its liquid crystal transition temperature or higher and then cooling below the liquid crystal transition temperature. When a block copolymer 40 is used having a hydrophobic polymer chain 41 having a liquid crystalline side chain having an azobenzene skeleton as a mesogenic group and a hydrophilic polymer chain containing polyethylene oxide (PEO), for example, it is preferred that the annealing treatment be carried out by heating to 100° C. or higher, which is its liquid crystal transition temperature, once and then cooling to 90° C., which is below the liquid crystal transition temperature and above its glass transition temperature.

(Constitution of Passage Route (Nanopore))

As schematically shown in FIGS. 2(a) and 2(b), microdomains formed by self-assembly of a block copolymer 40 have a periodic structure in which a number of domains are arranged with a fixed cycle. The periodic structure is derived from the principle of microphase separation that block copolymer molecules are phase-separated in molecular order.

In the meantime, in the DNA transport control device 10, it is required to transport a DNA strand 31 individually.

Therefore, in order to control the transport of a DNA strand 31, it is required that a passage route 14 (nanopore) be individually independently arranged at a predetermined position, or in order to use for parallel processing, it is required that passage routes be arranged at predetermined positions at a predetermined interval.

In the present invention, a passage route (s) 14 including a base material pore(s) 13 and a cylindrical microdomain(s) 22 individually arranged at a predetermined position or arranged at a predetermined interval is(are) formed according to the first or second embodiment described below.

First Embodiment

First, the first embodiment will be described appropriately with reference to FIGS. 5(a) to 5(d). According to the present embodiment, the first effect of the present invention, which is the delay in the transport of a DNA strand, and further the second effect, that the finer passage route than the size of a base material pore can be obtained, can be obtained at the same time.

As schematically shown in FIG. 1, FIGS. 2(a) and 2(b), the device 10 is obtained by producing a block copolymer thin film 20 with the above-mentioned features on a base material 11 having a base material pore 13 opened thereon in the transport of DNA according to the present invention.

In the first embodiment, as shown in FIGS. 5(a) to 5(d), the diameter D of a base material pore 13 is greater than the diameter d of cylindrical microdomains 22. As described above, the base material pore 13 can be processed by a top-down means typified by semiconductor microfabrication, and an opening can be arranged at an intended position. In the meantime, the diameter D of a base material pore to be obtained in a top-down means is restricted in terms of the processing technique, and it is thus difficult to obtain an opening with a diameter of single nano order with repeatability as described above. When the diameter D of a base material pore 13, the diameter d of cylindrical microdomains 22 and the center spacing L of cylindrical microdomains 22 have a relationship in Formula 1 below, however, cylindrical microdomains 22 are arranged on a base material pore 13 or in the inner portion thereof in a self-adjusting manner, and consequently a passage route 14 with a diameter smaller than that of the base material pore 13 can be obtained.

$$d<D<L \quad \text{Formula 1:}$$

Figure 5A:
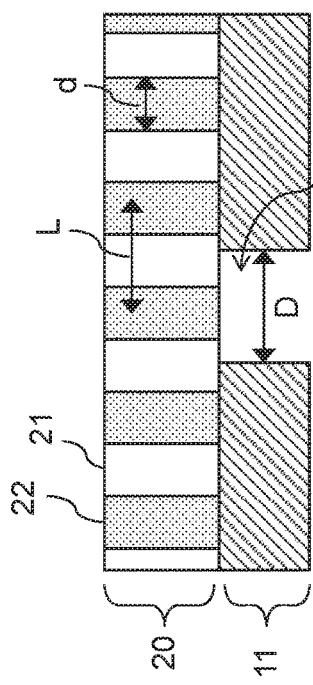
FIGS. 5A to 5G are schematic diagrams illustrating the cross-sectional structure of a DNA transport control device 10.

When the relationship of Formula 1 is satisfied, by producing a block copolymer thin film 20 on a base material pore 13 and self-assembling the thin film to form cylindrical microdomains 22 to penetrate the block copolymer thin film 20, as schematically shown in FIG. 5(a), a cylindrical microdomain 22 is arranged on the base material pore 13 in a self-adjusting manner. In this case, the centers of the base material pore 13 and the cylindrical microdomain 22 do not necessarily correspond to each other; however, a DNA strand is capable of passing through the passage route 14 including the cylindrical microdomain 22 and the base material pore 13 and any problems are not caused to the motion as a transport device.

Figure 5B:
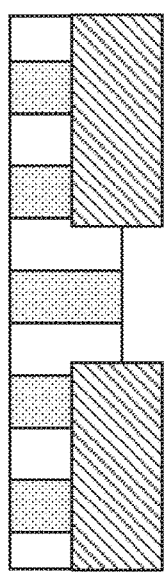
Figure 5C:
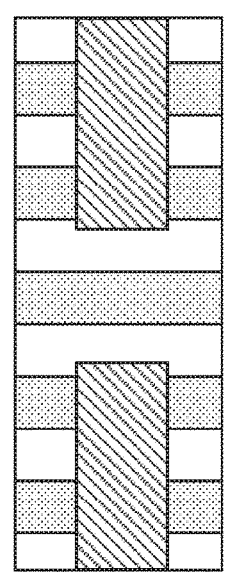
Figure 5D:
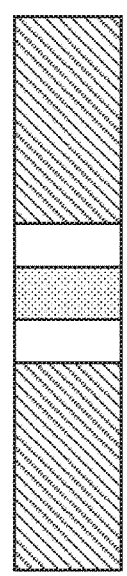

In addition, as other constitutions in which the relationship of Formula 1 is satisfied, FIGS. 5(b) to 5(d) can be also exemplified. FIG. 5(b) schematically illustrates a state in which a part of a block copolymer thin film 20 is also produced in the inner portion of the base material pore 13, FIG. 5(c) schematically illustrates a state in which a part of a block copolymer thin film 20 is produced on both surfaces of the base material pore 13, and FIG. 5(d) schematically illustrates a state in which a block copolymer thin film 20 is produced in the inner portion of the base material pore 13. When such constitutions are formed, the positions of the cylindrical microdomain 22 and the base material pore 13 are self-adjusted by the effect of the wall surface around the base material pore 13 so that the centers of the two may be equal.

According to this embodiment, a passage route 14 with a diameter smaller than the diameter D of a base material pore 13 can be easily obtained. The processing of the passage route 14 becomes easier, and costs involved in producing a DNA transport control device can be expected to decrease. Further, the size of a passage route 14 is prescribed by the diameter d of cylindrical microdomains 22, and thus dimensional repeatability is also very good.

When applying the first embodiment, the diameter d of cylindrical microdomains 22 is preferably 20 nm or less and particularly 10 nm or less so that multiple DNA strands will not enter a cylindrical microdomain at a time, and also preferably 1 nm or more and particularly 1.4 nm or more so that the entry of DNA strand may not be difficult.

The ratio D/d of the diameter D of a base material pore 13 and the diameter d of cylindrical microdomains 22 is preferably as high as possible. According to Formula 1, in order to increase the ratio D/d, it is required that the ratio L/d of the center-to-center spacing L of cylindrical microdomains 22 and the diameter d of cylindrical microdomains 22 be high. As described above, the L/d value is controlled by the phenomenon of the microphase separation of a block copolymer, and a greater value than usual can be obtained by applying a liquid crystalline block copolymer.

Second Embodiment

Next, the second embodiment of the present invention will be described appropriately with reference to FIGS. 5(e) to 5(g). Unlike in the first embodiment, in the second embodiment, the diameter D of a base material pore 13 is smaller than the diameter d of cylindrical microdomains 22.

$$d>D \quad \text{Formula 2:}$$

When the relationship of the formula 2 is satisfied, a base material pore 13 has a function of restricting DNA strands transported in a passage route 14 to a single molecule, and cylindrical microdomains 22 contribute to only a function of delaying the transport velocity of a DNA strand.

In the present embodiment, it is required to reduce the diameter of a base material pore 13 to a size which can restrict DNA strands passing at a time to a single molecule. However, compared with a solid-state nanopore without having cylindrical microdomains 22, the restriction of a pore diameter is relaxed. That is, in a common solid-state nanopore, it is required that the effect of delaying DNA transport velocity be also obtained by reducing its diameter, and therefore it is required that the pore diameter be 1 to 2 nm which is equal to the size of a molecule of DNA strand. In contrast, in the present embodiment, the effect of delaying a DNA strand can be expressed by cylindrical microdomains 22, and therefore it is only required that a base material pore 13 have a size which can restrict the number of DNA strands passing at a time to one, specifically 10 nm or less and particularly 3 nm or less.

The features of the present embodiment include being capable of reading a base sequence of DNA by a blockage current method. As shown in FIG. 1, when voltage is applied with a DNA transport control device immersed in an aqueous solution of a low molecular electrolyte typified by potassium chloride, ion current derived from the electrolyte passing through a nanopore flows. When a DNA strand is contained in an aqueous solution, an event that the DNA strand passes through the nanopore occurs. When the ion current in this case is measured, the electric current value varies depending on the type of base passing through the nanopore. A means for reading a base sequence from the amount of electric current change is a blockage current method. The blockage current method is an excellent method in terms of being not necessary to separately prepare a sensor to read sequences.

In order to read changes in electric current values by bases by the blockage current method at a resolution at which a base can be read, however, it is required that the thickness of a nanopore be equal to the length of a base. That is, it is required that not only the diameter of the nanopore be small but also the thickness be a few nano meters or less. When the diameter of a nanopore has distribution in the direction of thickness, it is required that the thickness of a portion with the least diameter be a few nano meters or less. A nanopore in such a very thin film can be produced by opening a pore in a very thin base material containing a material such as graphene as a base material. Even substances other than graphene can be used in the same manner as long as a base material with a few nanometer-thickness can be obtained by the substances. In addition, when a thicker base material is used, as long as the thickness of the edge of a nanopore can be thin in the same degree by processing, such a process can be similarly utilized.

In the meantime, when the thickness of an opening part in a base material is about a few nanometers, even if the diameter can be made to an ideal diameter which is equal to the diameter of a molecule of DNA strand, it is difficult to delay the transport velocity of a DNA strand to the velocity at which changes in electric current values can be measured. In the present invention, however, the action of delaying the transport velocity of a DNA strand can be obtained by using a hybrid containing a base material pore 13 in a base material 11 and a cylindrical microdomain 22 in a block copolymer thin film 20 as a passage route, and further changes in electric current values can be detected at a resolution at which a base can be read. The DNA transport control device according to the present embodiment is particularly useful for a DNA sequencing device by a blockage current method.

Figure 5E:
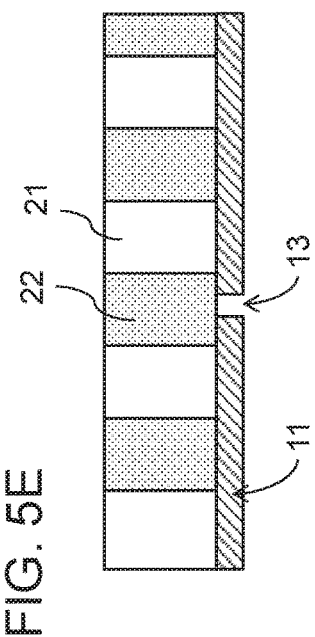
Figure 5F:
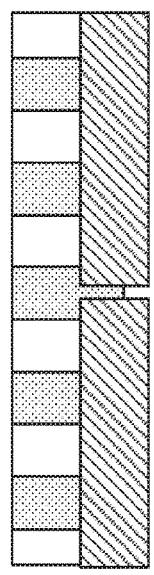
Figure 5G:
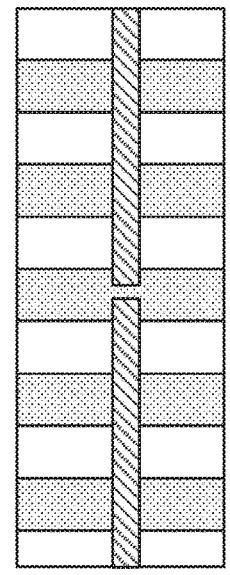

The constitutions in which the relationship of the formula 2 in the present embodiment is satisfied include those schematically shown in FIGS. 5(e) to 5(g). FIG. 5(e) schematically illustrates a state in which a block copolymer thin film 20 is produced on the surface of a base material 11 having a base material pore 13, FIG. 5(f) schematically illustrates a state in which a block copolymer thin film 20 is produced on the surface of a base material 11 and further in the inner portion of a base material pore 13, and FIG. 5(g) schematically illustrates a state in which a block copolymer thin film 20 is produced on both surfaces of a base material 11. Even in any of these constitutions, the above-mentioned effect can be similarly expressed.

In the present embodiment, when the diameter d of cylindrical microdomains 22 is too large, a hydrophilic polymer chain in the cylindrical microdomains is easily swollen, and the effect of delaying the transport of DNA is not sufficiently displayed. It is therefore preferred that the diameter d be 50 nm or less and particularly 30 nm or less, and it is also preferred that the diameter d be 5 nm or more and particularly 10 nm or more in terms of alignment of a base material pore 13 and a cylindrical microdomain 22 described below.

In the present embodiment, consideration is required to arrange a base material pore 13 and a cylindrical microdomain 22 in a relationship of 1:1. In the case of the above-described first embodiment, the base material pore 13 and cylindrical microdomains 22 can be arranged in a self-adjusting manner by satisfying Formula 1; however, in the case of the second embodiment, since Formula 1 is not satisfied, the alignment mechanism in a self-adjusting manner is not expressed. The method for solving this problem includes a method using a partition member and utilizing graphoepitaxy.

FIGS. 6(a) to 6(c) are diagrams describing a method for controlling the arrangement of cylindrical microdomains 22 using a partition member by graphoepitaxy. The graphoepitaxy herein means to control the arrangement of microdomains obtained by self-assembly of a block copolymer using a three-dimensional guide such as the wall surface of a partition member.

FIGS. 6(a) and 6(b) illustrate an example in which a partition member 15 is arranged to form a hexagonal hollow space on the surface of the base material 11. The cylindrical microdomains 22 are self-assembled in a hexagonally arranged state; however, when the wall surface of the partition member 15 exists, the cylindrical microdomains are arranged corresponding to the shape of the wall surface of the partition member 15, i.e. in a state in which the densest direction of the arranged grid formed by cylindrical microdomains 22 is along the wall surface. This is derived from the effect in which free energy is least when cylinders are closely filled in a restricted space. Therefore, when a hexagonal space exists as shown in FIG. 6(a), cylindrical microdomains 22 are arranged along each wall surface of the partition member 15. In this case, when the distance connecting the opposite apexes of the hexagonal space is designed to be a distance almost equal to an odd multiple of the center-to-center spacing L of cylindrical microdomains 22, a cylindrical microdomain 22 can be arranged in the center of the space. That is, when a base material pore 13 is arranged in the center of a hexagonal space, the base material pore 13 and a cylindrical microdomain 22 can be arranged at 1:1. The shape of the space is not necessarily restricted to a hexagon and can be a square or circle or the like.

Even when the space formed by a partition member has only wall surfaces without a hollow, the same graphoepitaxy effect is obtained. The arrangement of wall surfaces is only required to form a space in the shape of for example a hexagon, square or circle as is the case with the above. In addition, as shown in FIG. 6(c), wall surfaces one end or both ends of which are not closed can be used. In this case, as shown in FIG. 6(c), the arrangement in the direction parallel to the wall surfaces can be controlled by providing a notch 16 on the wall surfaces.

As other methods for controlling the arrangement of microdomains, there are a method utilizing an external field such as light and a method for chemically patterning the surface of a base material and the like, and the most suitable method can be applied depending on the design of a DNA transport control device. The above-mentioned methods for controlling an arrangement can be also used in combination with the first embodiment of the present invention. In this case, a base material pore and a cylindrical microdomain can be aligned with a higher degree of accuracy.

For producing a partition member, an existing semiconductor micromachining technique, for example photolithography and various direct drawing means, can be appropriately used. In addition, a material for the partition member is not particularly restricted and semiconductor materials such as silicon, metallic materials typified by gold and titanium, oxides and nitrides thereof and further organic substances such as polymers and resists can be appropriately used.

(Multipore DNA Transport Control Device)

As described above, in both the first embodiment and the second embodiment of the present invention, a base material pore 13 and a cylindrical microdomain 22 can be arranged at 1:1. By utilizing this feature, a multipore DNA transport control device with multiple passage routes 14 transporting a DNA strand arranged at optional positions can be obtained. Specifically, multiple base material pores 13 are provided at optional positions, and a block copolymer thin film is produced on the surface thereof, and cylindrical microdomains 22 are arranged to the base material pores at 1:1. In this case, various methods described above can be applied for aligning the base material pores 13 and cylindrical microdomains 22. That is, in the case of the first embodiment of the present invention, alignment in a self-adjusting manner or graphoepitaxy utilizing a partition member can be utilized. In addition, in the case of the second embodiment, graphoepitaxy utilizing a partition member can be utilized. According to a multipore DNA transport control device, the parallel processing for reading the sequence of a DNA strand can be achieved and the device is particularly effective for faster reading velocity.

EXAMPLES

The present invention will now be described in more detail by way of examples thereof. It should be noted however that the present invention is not limited to these examples.

Example 1: First Embodiment (1) Synthesis and Evaluation of Liquid Crystalline Block Copolymer For a block copolymer, PEO was used as a hydrophilic polymer chain and PEO-b-PMA(Az) containing a polymethacrylate derivative (PMA(Az)) having a liquid crystalline side chain having a mesogenic group based on azobenzene was used as a hydrophobic polymer chain. The chemical formula thereof is shown below:

where m and n in the chemical formula are natural numbers and represent the polymerization degree of PEO and PMA (Az).

PEO-b-PMA (Az) was polymerized by an atom transfer radical polymerization method in accordance with a method described in Y. Tian et al., Macromolecules 2002, 35, 3739-3747. The polymerization degree of the obtained block copolymer was evaluated by 1H NMR and GPC. The chemical composition of the polymerized PEO-b-PMA(Az) is as described in Table 1 below.

The self-assembled structure of the obtained PEO-b-PMA (Az) was evaluated. First, PEO-b-PMA(Az) was dissolved in toluene so that the concentration was 1.5 wt %, and the obtained solution was spin-coated on an Si wafer section on which an SiN thin film was produced, so that the film thickness was about 50 nm. In this case, the film thickness of PEO-b-PMA(Az) was measured by an optical thickness meter (F20 manufactured by FILMETRICS) and the film thickness was adjusted by changing the number of rotations during the spin-coating. When the number of rotations was about 3000 rpm, an intended film thickness was obtained.

Next, the obtained sample was introduced into a vacuum oven and subjected to thermal annealing treatment by the following method to self-organize the PEO-b-PMA(Az) thin film. First, the sample was put in vacuum and left for an hour in a heated state to 140° C. It was verified by the observation with a polarization microscope separately performed that PMA(Az), formed an isotropic phase at this temperature. Next, the sample was cooled to 90° C. to transfer PMA(Az)$_n$ from the isotropic phase to a smectic liquid phase. The sample was left for 3 hours in this state and then naturally cooled, and the self-assembly treatment was completed.

The self-assembled structure of the obtained sample was observed by a scanning electron microscope (SEM, S-4800 manufactured by Hitachi High-Technologies Corporation) or a transmission electron microscope (TEM, HF2200 manufactured by Hitachi High-Technologies Corporation). The observation was carried out after the PEO phase was stained by exposing the sample to Ru vapor. The examples of the obtained microscope images are shown in FIGS. 7(a) and 7(b).

Figure 7A:
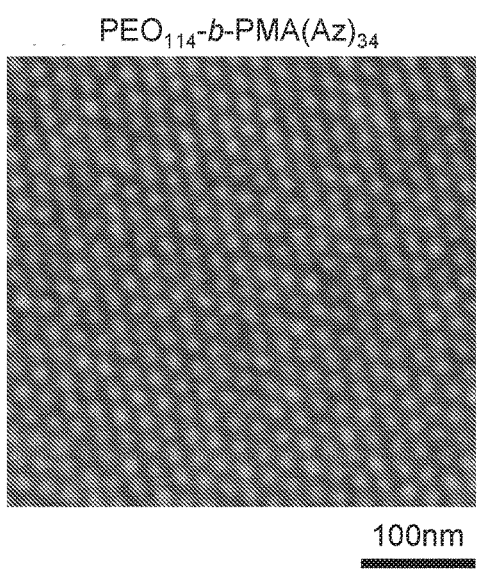
FIGS. 7A and 7B are electron microscope images of a thin film of PEO-b-PMA(Az).
Figure 7B:
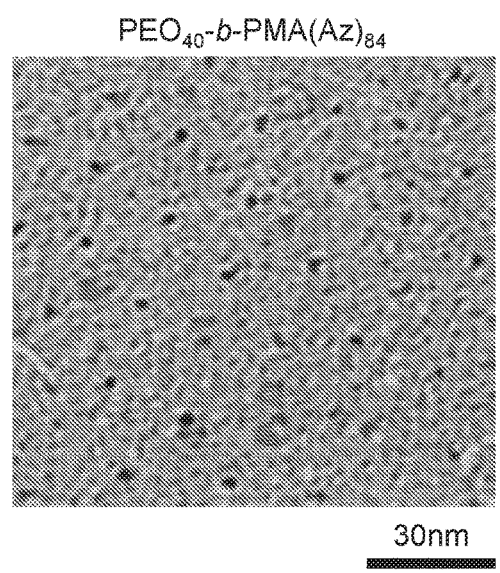

FIG. 7(a) is a SEM image of a thin film of PEO$_{114}$-b-PMA(Az)$_{34}$ and it was found that PEO cylindrical microdomains stained by Ru were arranged to form a hexagonal close-packed structure in a matrix containing PMA(Az). PEO stained by Ru generates more secondary electrons than PMA(Az) does, and thus PEO cylindrical microdomains, which are white, and PMA(Az) in the matrix, which is black, are observed according to SEM.

FIG. 7 (b) is a TEM image of a thin film of PEO$_{47}$-b-PMA(Az)$_{84}$ and it was found that PEO cylindrical microdomains stained by Ru were arranged to form a hexagonal close-packed structure in a matrix containing PMA(Az). It is

[Chemical Formula 1]

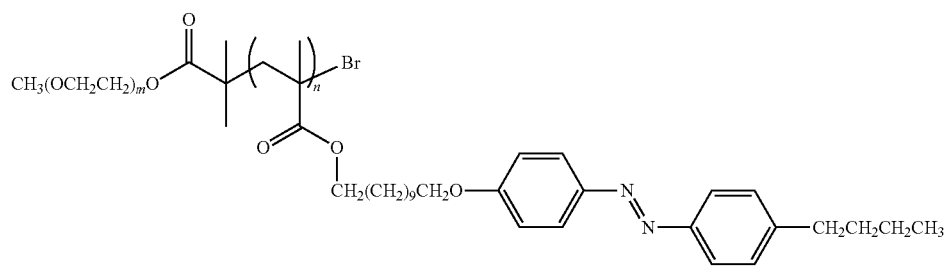

more difficult for electrons to permeate PEO stained by Ru than PMA(Az), and thus PEO cylindrical microdomains, which are black, and PMA(Az) in the matrix, which is white, are observed according to TEM.

PEO-b-PMA(Az) having other compositions was also evaluated in the same manner and the diameter d and center-to-center distance L of cylindrical microdomains containing PEO were measured by image processing of the obtained electron microscope images. The results are shown in Table 1.

TABLE 1

| Chemical Composition | Domain Shape | Domain Diameter d (nm) | Center-to-Center Distance L of Domains (nm) | L/d |
|---|---|---|---|---|
| $PEO_{40}$-b-$PMA(Az)_{14}$ | Cylinder | 3 | 13 | 4.3 |
| $PEO_{40}$-b-$PMA(Az)_{84}$ | Cylinder | 2 | 22 | 11.0 |
| $PEO_{114}$-b-$PMA(Az)_{34}$ | Cylinder | 9 | 23 | 2.6 |
| $PEO_{272}$-b-$PMA(Az)_{94}$ | Cylinder | 20 | 44 | 2.2 |

(2) Production of DNA Transport Control Device

A DNA transport control device was produced in accordance with a process schematically shown in FIGS. 8(a) to 8(d). First, an SiN thin film with a film thickness of 30 nm was produced on an Si wafer, a support substrate, and an SiN membrane window produced by removing a part of Si wafer by anisotropic etching was purchased and used as a base material (FIG. 8(a)). The opening part of the SiN thin film has side length of 250 μm. Next, a base material pore was opened in the SiN membrane in the opening part by the following method (FIG. 8(b)).

When the diameter of a base material pore was 15 nm or more, a focused ion beam system (FIB, FB2200 manufactured by Hitachi High-Technologies Corporation) was used to open the pore. As pore-processing conditions, a condition in which a pore of an intended size can be stably processed was detected by changing processing time and the number of repeats and applied. The confirmation of a pore shape and the evaluation of pore diameter were carried out by TEM observation. An example of the obtained base material pore is shown in FIG. 9(a).

When the diameter of a base material pore was 15 nm or less, the pore was opened by irradiating a focused electron beam to the SiN membrane using a scanning transmission electron microscope (STEM, HD2700 manufactured by Hitachi High-Technologies Corporation) at an accelerating voltage of 200 kV. The diameter of the pore was adjusted by changing the irradiating time of the electron beam. The pore state was confirmed by observing a bright field image using STEM used for processing.

Next, the film of PEO-b-PMA(Az) was produced on the surface of the base material having the base material pore opened thereon (FIG. 8(c)). First, PEO-b-PMA(Az) was dissolved in toluene so that the concentration was 1.5 wt %, and the obtained solution was spin-coated on the Si wafer section on which the SiN thin film was produced, so that the film thickness was about 40 nm. In this case, the film thickness of PEO-b-PMA(Az) was measured by an optical thickness meter (F20 manufactured by FILMETRICS) and the film thickness was adjusted by changing the number of rotations during spin-coating. When the number of rotations was about 3,000 rpm, an intended film thickness was obtained.

The obtained sample was subjected to thermal annealing treatment using a vacuum oven to self-assemble the thin film of PEO-b-PMA(Az). First, the sample was put in vacuum and left for an hour in a heated state to 140° C., and then cooled to 90° C. to transfer $PMA(Az)_n$ from the isotropic phase to a smectic liquid phase. The sample was left for 3 hours in this state and then naturally cooled, and the self-assembly treatment was completed (FIG. 8(d)).

DNA transport control devices of Sample Nos. 1-1 to 1-9 were produced in accordance with the specifications shown in Table 2. The obtained DNA transport control devices were observed using STEM (HD2700 manufactured by Hitachi High-Technologies Corporation) and the arrangement state of a base material pore and cylindrical microdomains were confirmed. By using STEM, a bright field image by a transmission electron detector is observed, and simultaneously an image by a secondary electron detector is also obtained, and an image (overlay image) obtained by electronically overlaying the images can be produced. The information on a base material pore is obtained from the bright field image and the information on the arrangement of cylindrical microdomains is obtained from the secondary electron image, and thus by overlaying the two images, the state of the alignment of the base material pore and the cylindrical microdomains can be known.

An example of the obtained overlay image is shown in FIG. 9(b). In this figure, a sample produced in accordance with the specification of Sample No. 1-2 in Table 2 was observed. It was verified by the obtained image that a cylindrical microdomain was arranged in the center of the base material pore (shown by the dot line for clarification) in a self-adjusting manner in a relationship of 1:1. The other samples were evaluated in the same manner, and the arrangement state of a base material pore and cylindrical microdomains containing PEO were observed, and a positional relationship between the base material pore and cylindrical microdomains and the number of cylindrical microdomains arranged on the base material pore were evaluated.

The obtained results are summarized in Table 2. In the samples with a relationship that the diameter d of cylindrical microdomains containing PEO is small compared with the diameter D of a base material pore and the center-to-center distance L thereof is great compared with the diameter D of the base material pore, i.e. the samples satisfying the relationship of Formula 1, d<D<L (Sample Nos. 1-1, 1-2, 1-5 and 1-6), it was found that the base material pore and cylindrical microdomain were arranged in a self-adjusting manner in a relationship of 1:1. In contrast, in the samples which do not satisfy the relationship of Formula 1 (Sample Nos. 1-3, 1-4, 1-7, 1-8 and 1-9), multiple cylindrical microdomains were arranged with respect to a base material pore.

The above results proved that, when cylindrical microdomains were formed to satisfy the relationship of Formula 1, a base material pore and a cylindrical microdomain could be arranged in a relationship of 1:1, and a DNA transport control device with a finer DNA passage route could be easily produced.

(3) Evaluation of Transport of DNA Strand by DNA Transport Control Device

The DNA transport control device produced by the above-mentioned method was installed in a flow cell produced with an acrylic resin. The flow cell had solution cells (volume 90 μl) on both sides of the DNA transport control device and a flow passage to introduce a liquid into the inner portion was equipped in the solution cells. In addition, an Ag/AgCl electrode was installed in each solution cell.

A DNA sample dissolved in a buffer solution with a concentration of 2 nM was introduced into one solution cell through the flow passage and a buffer solution was introduced into another cell. As the DNA sample, a double-stranded DNA (dsDNA, base length 1 k, NoLimits manufactured by Fermentas) or a single-stranded DNA (ssDNA, base length 5 k, polydeoxyadenylic acid) was used. In addition, as the buffer, a mixed solution of 1 M KCl, 10 mM Tris-HCl and 1 mM EDTA was adjusted to pH 7.5 and used.

A voltage was applied between electrodes by a patch clamp amplifier (Axopatch 200B manufactured by Axon instruments) and changes in ion current flowing between the electrodes with time were measured. The signals were digitized using an AD converter (NI USB-6281 manufactured by National instruments) at a sampling frequency of 50 kHz after removing a high-frequency component (cutoff frequency 2 kHz) by a low-pass filter and recorded.

Figure 10:
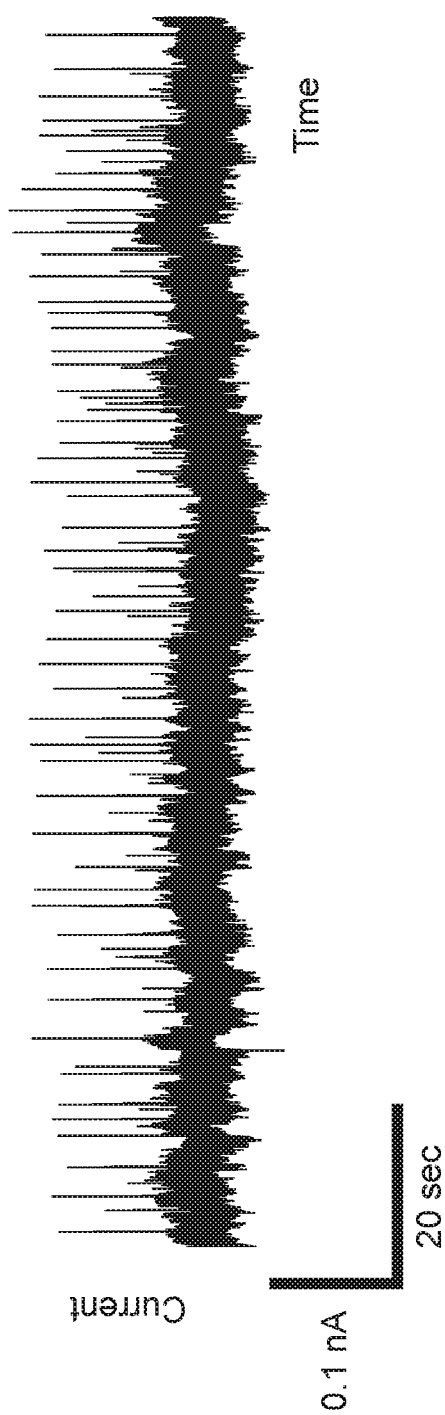
FIG. 10 is a diagram plotting ion current values observed when a buffer solution containing a dsDNA strand is used as a sample with respect to time.

FIG. 10 is a diagram plotting ion current values observed when a buffer solution containing a dsDNA strand was used as a sample with respect to time. As a DNA transport control device, one in which the diameter D of a base material pore was 21 nm and the diameter d of cylindrical microdomains was 9 nm was used (Sample No. 1-2 in Table 2). The voltage applied between electrodes was 700 mV. In the diagram shown in FIG. 10, spike peaks were observed on the ion current constantly flowing as a base. The spikes are derived from changes in ion current when a dsDNA strand passes through the passage route in the DNA transport control device.

Figure 11B:
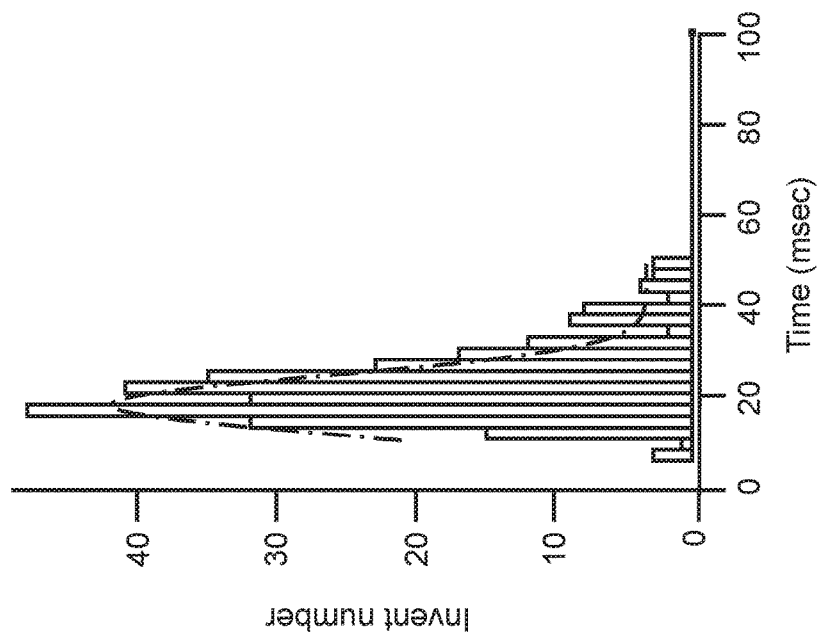
FIGS. 11A and 11B are an enlarged view of ion current spikes by the passage of a dsDNA strand and a duration distribution chart of the spikes.
Figure 11A:
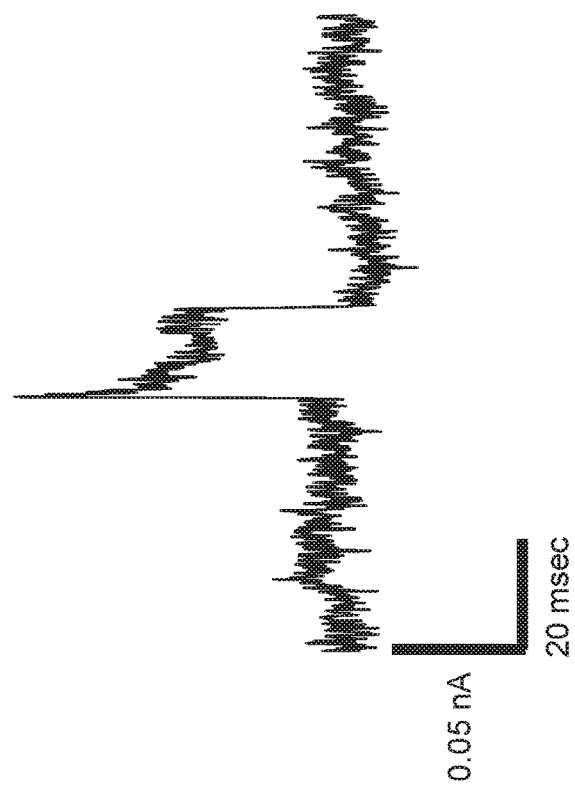

An example for which the spikes on ion current are measured by increasing time resolution is shown in FIG. 11($a$). From these measurement results, the duration of each spike was evaluated, and the time required for a DNA strand to pass through a passage route was measured. The distribution chart created by measuring the duration at a number of spikes is shown in FIG. 11($b$). It was found from FIG. 11($b$) that the duration of spikes was normally distributed. When the duration at the greatest frequency was obtained, the value was 18 msec, and it was found that the time required for a dsDNA strand to pass through the passage route in the DNA transport control device was on average 18 msec. Because the used dsDNA strand had a base length of 1 k, it was found that the passage time per base was 18 μsec/base.

The same experiment was carried out using a buffer solution containing a ssDNA strand as a sample. Consequently, it was found that the time required for one ssDNA strand to pass was on average 34 msec. Because the used ssDNA strand had a base length of 5 k, it was found that the passage time per base was 7 μsec/base.

As a DNA transport control device, one was used in which the diameter D of a base material pore was 21 nm and the diameter d of cylindrical microdomains was 2 nm (Sample No. 1-6 in Table 2), and the passage time of a ssDNA strand was measured in the same manner as in the above-mentioned method. Consequently, the passage time per base of ssDNA strand was 100 μsec/base. The other DNA transport control devices were also measured in the same manner and the results were summarized in Table 2.

In samples in which the number of microdomains constituting a DNA passage route, i.e. the number of cylindrical microdomains arranged in a base material pore, is 1, the passage time of a DNA strand could be clearly measured (Sample Nos. 1-1, 1-2, 1-5 and 1-6 in Table 2). In contrast, in samples in which the number of cylindrical microdomains arranged in a base material pore was 3 (Sample Nos. 1-3, 1-7 and 1-9), the passage time of a DNA strand could be evaluated in some cases, but the distribution of passage time was high and it was difficult to carry out the measurement with high reliability. It is believed that this was because, due to the existence of multiple passage routes for DNA, DNA strands passed through different cylindrical microdomains at the same time.

In samples in which the number of constituent cylindrical microdomains arranged in a base material pore was 7 (Sample Nos. 1-4 and 1-8 in Table 2), the frequencies with which spike peaks were observed by the passage of a DNA strand in the measurement of ion current values became very low. In contrast, a state in which ion current values corresponding to peaks were constantly consistently observed was obtained, and the passage time of a DNA strand could not be evaluated. It is believed that this is because, due to the existence of a number of passage routes for DNA strands, a number of DNA strands continuously passed through the DNA transport control device. The above results found that in order to control the transport of a DNA strand with repeatability and measure the passage time of DNA, it was required to produce a DNA transport control device to satisfy the relationship of Formula 1.

A DNA transport control device in which a pore with a diameter D of 9 nm was processed in a thin film containing SiN by STEM, which consisted only of a base material pore (solid-state pore) and did not have a block copolymer thin film layer was prepared as a control (Sample 2-1 in Table 2), and the DNA strand transport was evaluated in the same method as above. Consequently, the passage time per base of dsDNA strand was on average 0.1 μsec/base, and the passage time per base of ssDNA strand was on average $1.0 \times 10^{-4}$ μsec/base. Similarly, a DNA transport control device in which a pore with a diameter D of 2 nm was processed by STEM, which consisted only of a solid-state pore and did not have a block copolymer thin film layer was prepared (Sample 2-2 in Table 2), and the DNA strand transport was evaluated in the same method as above. Consequently, the passage time per base of ssDNA strand was on average 0.1 μsec/base.

When Sample No. 1-2 (with one cylindrical microdomain formed by a block copolymer) and Sample No. 2-1 (not having a block copolymer thin film layer), which both had a DNA passage route with a diameter of 9 nm, were compared, for example, the passage time of dsDNA strand was 18 μsec/base and 0.1 μsec/base respectively, and it is found that the passage time of DNA could be increased by 180-fold by forming a cylindrical microdomain. In addition, in the case of a ssDNA strand, a much greater delaying effect could be obtained, and it was found that the passage time could be increased by 4 digits or more by a cylindrical microdomain formed by a block copolymer. The same effect was also revealed by comparing Sample No. 1-6 (having one cylindrical microdomain formed by a block copolymer) and Sample No. 2-2 (not having a block copolymer thin film layer), both of which had a DNA passage route with a diameter of 2 nm.

From the above results, it is found that a DNA transport control device having cylindrical microdomains formed by a block copolymer can considerably delay the transport velocity of a DNA strand compared with a device containing only a solid-state pore.

TABLE 2

Constitution of DNA Transport Control Device

| Sample No. | Base Material Diameter of Passage Route (nm) | Cylindrical Microdomain Pore Diameter D (nm) | Cylindrical Microdomain Diameter d (nm) | Cylindrical Microdomain Center Spacing L (nm) | Number of Microdomains Arranged in Base Material Pore | Passage Time Per Base of DNA Strand (μsec/base) dsDNA (1k) | Passage Time Per Base of DNA Strand (μsec/base) ssDNA (5K) | Remarks |
|---|---|---|---|---|---|---|---|---|
| 1-1 | 9 | 15 | 9 | 23 | 1 | 18 | 7 | First Embodiment |
| 1-2 | 9 | 21 | 9 | 23 | 1 | 18 | 7 | First Embodiment |
| 1-3 | 9 | 40 | 9 | 23 | 3 | 18 to 56 | 7 to 15 | Comparative Example |
| 1-4 | 9 | 60 | 9 | 23 | 7 | Non-Evaluable | Non-Evaluable | Comparative Example |
| 1-5 | 2 | 15 | 2 | 22 | 1 | — | 100 | First Embodiment |
| 1-6 | 2 | 21 | 2 | 22 | 1 | — | 100 | First Embodiment |
| 1-7 | 2 | 40 | 2 | 22 | 3 | — | 100 to 350 | Comparative Example |
| 1-8 | 2 | 60 | 2 | 22 | 7 | Non-Evaluable | Non-Evaluable | Comparative Example |
| 1-9 | 3 | 21 | 3 | 13 | 3 | Non-Evaluable | Non-Evaluable | Comparative Example |
| 2-1 | 9 | 9 | None | None | — | 0.1 | $1 \times 10^{-4}$ | Control |
| 2-2 | 2 | 2 | None | None | — | — | 0.1 | Control |

Example 2: Another Mode of First Embodiment

A DNA transport control device with another structure was produced by the same method as in Example 1 (2) and the transport of a DNA strand was evaluated.

(1) Production of DNA Transport Control Device

First, a DNA transport control device was produced in accordance with a process schematically shown in FIGS. 8(a), 8(b), 8(c') and 8(d'). The same base material as in Sample No. 1-2 in Table 2 (the diameter D of the base material pore=21 nm) was prepared (FIGS. 8(a) and 8(b)), and a thin film of $PEO_{114}$-b-$PMA(Az)_{34}$ was produced on the base material so that the thickness might be thinner than in Example 1, 5 nm (FIG. 8(c')). Next, the obtained sample was subjected to thermal annealing treatment in the same manner as in Example 1 to self-assemble the thin film of $PEO_{114}$-b-$PMA(Az)_{34}$, and a cylindrical microdomain with a diameter of 9 nm (FIG. 8(d')) was formed.

When the obtained DNA transport control device was observed by SEM and STEM, as schematically shown in FIG. 8 (d'), it was verified that a cylindrical microdomain containing PEO was formed only in the base material pore. It was also verified that the cylindrical microdomain was arranged almost in the center of the base material pore at 1:1. It was verified that the remaining film of $PEO_{114}$-b-PMA $(Az)_{34}$ scatteredly existed in the surrounding area; however, a clear phase separation structure was not verified in the inner portion thereof. It is believed that this is because, by the dewetting of the very thin film of $PEO_{114}$-b-$PMA(Az)_{34}$ from the surface of the base material in the thermal annealing process, a part thereof flowed into the base material pore and the rest scatteredly remained on the surface of the base material.

(2) Evaluation of Transport of DNA Strand by DNA Transport Control Device

By using a device produced as above, the transport of a DNA strand was evaluated in the same manner as in Example 1. Consequently, as is the case with Example 1, the passage time per base of dsDNA strand (base length 1 k) was 18 μsec/base, and the passage time per base of ssDNA strand (base length 5 k) was 7 μsec/base, and these values were very high values compared with those of DNA transport control devices containing only a solid-state pore (Sample Nos. 2-1 and 2-2).

From the above results it is found that in the present mode, the transport velocity of a DNA strand could be considerably delayed compared with a device containing only a solid-state pore.

Example 3: Second Embodiment

A DNA transport control device in the second embodiment in which the diameter D of a base material pore was smaller than the diameter d of cylindrical microdomains unlike the first embodiment was produced and the transport of a DNA strand was evaluated.

(1) Production of DNA Transport Control Device

A DNA transport control device was produced in accordance with a process schematically shown in FIGS. 12(a) to 12(e). An Si wafer obtained by laminating an $SiO_2$ thin film (thickness 40 nm) and an SiN thin film (thickness 10 nm) was prepared, and resists were produced on both sides thereof, and patterning was carried out. Here, the resist on the back of the Si wafer was used to open a window on the Si wafer by anisotropic etching of the Si wafer, and the resist on the surface of the upper $SiO_2$ was used for patterning of $SiO_2$. FIG. 12(a) illustrates a cross-sectional view of a state in which after patterning of resists on both sides, a window with a side length of 50 μm was opened on the Si wafer by a KOH aqueous solution.

Next, as shown in FIG. 12 (b), the resist on the upper side of the $SiO_2$ thin film was used as a mask, and etching was carried out by buffered hydrofluoric acid, and a partition member containing $SiO_2$ was formed on the surface of SiN, a base material. Here, the shape of the partition member was in the shape of an exact hexagon with 110 nm on a side (the distance between opposite apexes 220 nm) as schematically shown in FIG. 6(a). After processing, the resists remaining on both sides were removed.

Next, as shown in FIG. 12 (c), a focused electron beam was irradiated at an accelerated voltage of 200 kV using STEM (HD2700 manufactured by Hitachi High-Technologies Corporation) to open a base material pore with a diameter of 2 nm in the SiN base material. In this case, processing conditions were determined by optimization obtained by changing irradiating conditions for an SiN membrane with the same film thickness separately prepared. In addition, the center of the exact hexagon formed by the wall surface of the partition member was used as the position of the base material pore.

Next, as shown in FIG. 12(d), PEO-b-PMA(Az) was produced on the surface of the SiN base material in the same manner as in Example 1. In this case, $PEO_{272}$-b-$PMA(Az)_{94}$ with a high molecular weight was used as PEO-b-PMA(Az). As shown in Table 1, $PEO_{272}$-b-$PMA(Az)_{94}$ is self-assembled to form cylindrical microdomains containing PEO with a diameter d of 20 nm in a matrix containing PMA(Az) so that the center spacing L will be 44 nm. The film of $PEO_{272}$-b-$PMA(Az)_{94}$ was produced on the surface of $SiO_2$, a partition member, by a spin-coating method so that the film thickness was about 20 nm. In this case, the inner portion of the space surrounded by the partition member, i.e. the film thickness on the surface of SiN, was believed to be about 30 nm. The spacing between the opposite apexes of the hexagonal space surrounded by the partition member, 220 nm, was 5 times, i.e. an odd multiple, the center spacing of cylindrical microdomains, 44 nm.

Further, as shown in FIG. 12(e), the $PEO_{272}$-b-$PMA(Az)_{94}$ was self-assembled by the thermal annealing treatment in the same manner as in Example 1 to form cylindrical microdomains in the inner portion of the exact hexagonal space surrounded by the partition member.

When the obtained sample was observed by SEM and STEM, it was verified that the same structure as schematically shown in FIG. 6(a) was formed in the inner portion of the hexagonal space surrounded by the partition member. That is, it was verified that by graphoepitaxy using the hexagonal partition member as a guide, three cylindrical microdomains were arranged on a side of the hexagon, a cylindrical microdomain with a diameter d of 20 nm was exactly arranged in the center of the hexagon, and the base material pore opened with a diameter D of 2 nm and the cylindrical microdomain were exactly aligned in the center of the hexagonal space at 1:1.

It was verified that $PEO_{272}$-b-$PMA(Az)_{94}$ was uniformly filled in the inner portion of the hexagonal space. It is believed that this is because $PEO_{272}$-b-$PMA(Az)_{94}$ flowed into the inner portion of the hexagonal space from the surface of the surrounding partition member in the annealing process, and the film thickness of $PEO_{272}$-b-$PMA(Az)_{94}$ in the inner portion of the hexagonal space was about 40 nm which was equal to the film thickness of $SiO_2$. The remaining droplet-like film of PEO-b-PMA(Az) was verified on the surface of the partition member ($SiO_2$ thin film) in the surrounding of the hexagonal space, and this was predicted to result from dewetting of the PEO-b-PMA(Az) remaining the surface of the partition member.

(2) Evaluation of Transport of DNA Strand by DNA Transport Control Device

By using a device produced by the above-mentioned method, the transport of a DNA strand was evaluated in the same manner as in Examples 1 and 2. Consequently, the passage time per base of ssDNA strand (base length 5 k) was 9 μsec/base. In contrast, when the measurement was carried out using a sample containing only a base material pore obtained by the procedure until FIG. 12(c), the passage time per base of ssDNA strand (base length 5 k) was $1 \times 10^{-4}$ μsec/base. That is, it was found that even when a pore had an identical size, the passage time was considerably delayed by $9 \times 10^4$ times by arranging a cylindrical microdomain at 1:1.

Example 4: Another Mode of Second Embodiment

A DNA transport control device having another structure was produced by the same method as in Example 3 (1) and the transport of a DNA strand was evaluated.

(1) Production of DNA Transport Control Device

A DNA transport control device was produced in accordance with a process schematically shown in FIGS. 12(a) to 12(c), 12(d') and 12(e'). A base material pore with a diameter D of 2 nm was opened on an SiN thin film with a thickness of 10 nm in the same manner as in Example 3 until FIG. 12(c). Next, as shown in FIG. 12(d'), the same $PEO_{272}$-b-$PMA(Az)_{94}$ film as in Example 3 was produced on the surface of $SiO_2$, a partition member, by a spin-coating method so that the film thickness was 40 nm which is twice that in Example 3. After that, thermal annealing was carried out in the same manner as in Example 3 and the thin film of $PEO_{114}$-b-$PMA(Az)_{34}$ was self-assembled to form cylindrical microdomains with a diameter d of 20 nm.

When the obtained sample was observed by SEM and STEM, it was observed that cylindrical microdomains were uniformly arranged not only in the inner portion of the hexagonal space but also on the surface of the partition member and formed. In addition, when a positional relationship between the base material pore, the wall surface of the partition member and the cylindrical microdomains was observed from an overlay image of a transmission bright field image and a secondary electron image by STEM, it was verified that as shown in the cross-sectional image of FIG. 12(e'), the arrangement of cylindrical microdomains was restricted along the wall surface of the partition member and the base material pore and a cylindrical microdomain were exactly aligned in the center of the hexagonal space at 1:1.

(2) Evaluation of Transport of DNA Strand by DNA Transport Control Device

Using a device produced by the above-mentioned method, the transport of a DNA strand was evaluated in the same manner as in Examples 1 to 3. Consequently, the passage time per base of ssDNA strand (base length 5 k) was 12 μsec/base. This value was slightly high compared with that of a device in Example 3, and it is believed that this is because, in the device constitution in Example 4, the height of a cylindrical microdomain constituting a passage route is high compared with that in Example 3, and the greater delaying effect was obtained.

The above results found that in the present mode, the transport velocity of a DNA strand could be considerably delayed compared with a device containing only a solid-state pore.

REFERENCE SIGNS LIST

10 DNA transport control device
11 base material
12 support substrate
13 base material pore
14 passage route
15 partition member 16 notch
20 block copolymer thin film
21 matrix
22 cylindrical microdomain
30 solution cell
31 DNA strand
32 electrode
33 electrolyte solution
40 block copolymer
41 hydrophobic polymer chain
42 hydrophilic polymer chain
43 fixing point
51 SiN thin film
52 silicon wafer
53 thin film of PEO-b-PMA(Az)
54 PMA(Az) matrix
55 PEO cylindrical microdomain
56 remaining film of PEO-b-PMA(Az)
57 $SiO_2$ thin film
58 resist The entire publications, patents and patent applications cited in the present description are directly incorporated herein by reference.

The invention claimed is:

1. A DNA transport control device having a nanopore which allows the passage of only a single molecule of DNA strand,
    the device comprising: a base material having an opening; and a thin film of a block copolymer formed on the base material,
    wherein the thin film includes microdomains which are formed by self-assembly of the block copolymer and penetrate the thin film, and a matrix surrounding the microdomains, and the nanopore includes one opening in the base material and a single microdomain, and
    wherein the block copolymer comprises a hydrophilic polymer chain and a hydrophobic polymer chain, wherein the hydrophobic polymer chain has a liquid crystalline side chain.

2. The DNA transport control device according to claim 1, wherein the microdomains and the matrix surrounding the microdomains are formed by the hydrophilic polymer chain and the hydrophobic polymer chain, respectively.

3. The DNA control device according to claim 2, wherein the hydrophilic polymer chain contains polyethylene oxide, polylactic acid, polyhydroxyalkylmethacrylate or nucleic acid.

4. The DNA control device according to claim 2, wherein the hydrophobic polymer chain has a structure in which the alkyl moiety in polyalkylmethacrylate is partially or completely substituted with a liquid crystalline side chain.

5. The DNA transport control device according to claim 1, wherein the microdomains are cylindrical.

6. The DNA transport control device according to claim 5, wherein the diameter D of the opening in the base material is greater than the diameter d of the cylindrical microdomains and smaller than the center-to-center distance L of the cylindrical microdomains.

7. The DNA control device according to claim 5, wherein the diameter D of the opening in the base material is smaller than the diameter d of the cylindrical microdomains.

8. The DNA control device according to claim 1, further having a partition member provided on the base material, wherein the microdomains have an arrangement corresponding to the shape of the partition member.

9. A DNA sequencing device comprising: a DNA transport control device according to claim 1; two solution cells communicated via a nanopore in the DNA transport control device; and electrodes provided in each solution cell to apply voltage between the two solution cells.

10. The DNA sequencing device according to claim 9, comprising a sensor to read a DNA strand passing through the nanopore in the inner portion or the neighborhood of the DNA transport control device.

11. A method for producing a DNA transport control device having a nanopore which allows the passage of only a single molecule of DNA strand,
    the method comprising the steps of:
    preparing a base material having an opening,
    producing a thin film of a block copolymer on the base material, and
    forming a nanopore including one opening in the base material and a single microdomain by forming microdomains penetrating the thin film and a matrix surrounding the microdomains by self-assembly of the block copolymer,
    wherein the microdomains formed by the self-assembly of the block copolymer are cylindrical, which method comprises, after measuring the diameter and the center-to-center distance thereof, determining the size of an opening in the base material based on the values.

12. The method according to claim 11, further comprising the step of providing a partition member on the base material, and comprising aligning an opening in the base material and microdomains by forming the microdomains along the partition member.

* * * * *